United States Patent [19]

Derynck et al.

[11] Patent Number: 4,742,003
[45] Date of Patent: May 3, 1988

[54] HUMAN TRANSFORMING GROWTH FACTOR

[75] Inventors: Rik M. A. Derynck, Burlingame; David V. Goeddel, Hillsborough, both of Calif.

[73] Assignee: Genentech, Inc., South San Francisco, Calif.

[21] Appl. No.: 695,494

[22] Filed: May 14, 1985

Related U.S. Application Data

[63] Continuation-in-part of Ser. No. 581,743, Feb. 17, 1984, abandoned.

[51] Int. Cl.$^4$ .................. C12P 21/00; C12P 21/02; C12N 15/00; C12N 1/00
[52] U.S. Cl. .................. 435/68; 435/70; 435/172.3; 435/255; 530/324; 530/350; 530/828; 935/13; 935/28; 935/29; 935/57; 935/47; 935/48
[58] Field of Search ............ 435/68, 172.3, 317, 435/70, 255; 260/112 R, 112 B; 536/27; 935/13, 27, 48, 29, 47, 56, 63, 73, 78; 514/12, 2; 530/324, 350, 828

[56] References Cited

U.S. PATENT DOCUMENTS

| | | | |
|---|---|---|---|
| 4,338,397 | 7/1982 | Gilbert et al. | 435/68 |
| 4,358,586 | 11/1982 | Rubin | 536/27 |
| 4,511,503 | 4/1985 | Olsen et al. | 260/112 R |
| 4,546,082 | 10/1985 | Kurjan et al. | 435/172.3 |

OTHER PUBLICATIONS

Itakura et al., *Science*, vol. 198, pp. 1056-1063, 1977, "Expression in *Escherichia coli* of a Chemically Synthesized Gene for the Hormone Somatostatin".
Derynck et al., *Cell*, vol. 38 (1), pp. 287-297, Aug. 1984, "Human Transformig Growth Factor-Alpha: Precursor Structure and Expression in *E. coli*".
Derynck et al., *Nature*, vol. 316, pp. 701-705, 1985, "Human Transforming Growth Factor-beta Complementary DNA Sequence and Expression in Normal and Transformed Cells".
Derynck et al., *Cancer Cells*, vol. 3, (Growth Factors Transform.), pp. 79-86, "Human Transforming Growth Factor-Alpha: Precursor Sequence, Gene Structure and Heterologous Expression".
Tame et al. *Proc. Natl. Acad. Sci.*, vol. 83 (21), pp. 8082-8086, 1986, "Efficient Synthesis of Human Type Alpha Transforming Growth Factor: Its Physical and Biological Characterization."
Marguardt et al., *Proc. Natl. Acad. Sci.*, vol. 80, pp. 4684-4688, Aug. 1983, "Transforming Growth Factors Produced by Retrovirus Transformed Rodent Fibroblust and Human Melanoma Cells: Amino Acid Sequence Homology with Epidermal Growth Factor.
Marguardt et al., *J. Biol. Chem.*, vol. 257 (9), May 10, 1982, pp. 5220-5225, "Human Transforming Growth Factor".
Toduro et al., *Proc. Natl. Acad. Sci.*, vol. 77 (9), pp. 5258-5262, Sep. 1980, "Transforming Growth Factors Produced by Certain Human Tumor Cells: Polypeptides that Interact with Epidermal Growth Factor Receptors."
Anzano et al., *Proc. Natl. Acad. Sci.,* vol. 80, pp. 6264-6268, Oct. 1983, "Surcoma Growth Factor From Conditioned Medium of Virally Transformed Cells is Composed of both Type $\alpha$ and Type $\beta$ Transforming Growth Factors."
Kemp et al., "P/N.A.S. USA" 78(7): 4520-4524, (Jul. 1981).
Taniguchi et al., "P.N.A.S. USA" 77(9): 5230-5233, (Sep. 1980).
Maniatis, T., "Molecular Cloning, A Laboratory Manual" Cold Springs Harbor Lab., Summary 433, (1982).
Roberts, T. M., "Promoters, Structure & Function" Rodriguez et al., Ed. 452-461, (1982).
Ohsuye, K., et al., "Nucl. Acids Res." 11(5): 1283-1295, (1983).
Kadonaga, J., et al., "J. Biol. Chem." 259(4): 2149-2154, (1984).
Roberts, A., et al., "P.N.A.S. USA" 77(6): 3494-3498, (Jun. 1980).
Sporn, M., et al., "Molecular Actions and Targets for Cancer Chemotherapeutic Agents" Sartorelli, A., et al., Ed. 542-554, (1981).

*Primary Examiner*—Thomas G. Wiseman
*Assistant Examiner*—Robin Lyn Teskin

[57] ABSTRACT

Methods and compositions are provided for the recombinant synthesis of the tumor growth factor-$\alpha$ precursor and its fragments. These are useful in therapy and diagnosis, as are antibodies raised by immunization with the tumor growth factor-$\alpha$ precursor and its fragment.

11 Claims, 13 Drawing Sheets

Synthesized olignucleotide probes 48 mer: 5' GTT GTT TCT CAC TTC AAC AAA TGC CCA GAC TCC CAT ACC CAG TTC TGC

1A-D:  AA$^A_G$ TT$^A_G$ TT$^C_T$ AC$^G_A$ GG -5'

41 mer: 5' AC CAG GAA GCG GCA GGT GCC GTG GAA GCA GAA CTG GGT ATG

2A-D:  5' CC G$_A$TG AAA A$_G$CA $^A_G$AA

Fig. 1.

```
                                              ↓ ala asp pro val ala ala ala VAL VAL
GAT CTG AGC CCT GCA TCT TTC CTC TCC CCA GAC GCA GAC CCG GTG GCT GCA GCA GTG GTG
↑
Sau3AI
                                                                              ↑
                                                                             PstI
SER HIS PHE ASN ASP CYS ASP SER HIS THR GLN PHE CYS PHE HIS GLY THR CYS ARG
TCC CAT TTT AAT GAC TGC CCA GAT TCC CAC ACT CAG TTC TGC TTC CAT GGA ACC TGC AGG
                                                        ↑                       ↑
                                                       NcoI                    PstI ↓ VAL oc
PHE LEU VAL GLN GLU ASP LYS PRO ALA CYS
TTT TTG GTG CAG GAG GAC AAG CCA GCA TGT GTG TAA GTA TCC CCT GTT CTC CTG GAG ATC
                                                                              ↑
                                                                            BglII
```

```
GGGGGGGGGGGAGGCTGGAGAGCCTGCCCCGCCCCGTAAA ATG GTC CCC TCG GCT GGA CAG CTC GCC CTG TTC GCT CTG GGT ATT GTG TTG GCT
                                         Met Val Pro Ser Ala Gly Gln Leu Ala Leu Phe Ala Leu Gly Ile Val Leu Ala
                                          1                                  10
```

```
Ala Cys Gln Ala Leu Glu Asn Ser Thr Ser Pro Leu Ser Ala Asp Pro Pro Val Ala Ala Ala Val Val Ser His Phe Asn Asp Cys Pro
GCG TGC CAG GCC TTG GAG AAC AGC ACG TCC CCG CTG AGT GCA GAC CCC CCC GTG GCT GCA GCA GTG GTG TCC CAT TTT AAT GAC TGC CCA
 20                           30                                 40         ↑                              50
                                                                             150
                                                                             Pst 1
```

```
Asp Ser His Thr Gln Phe Cys Phe His Gly Thr Cys Arg Phe Leu Val Gln Glu Asp Lys Pro Ala Cys Val Cys His Ser Gly Tyr Val
GAT TCC CAC ACT CAG TTC TGC TTC CAT GGA ACC TGC AGG TTT TTG GTG CAG GAG GAC AAG CCA TGT GTC TGC CAT TCT GGG TAC GTT
         60               ↑                    ↑                70                            250
                          200                  Pst 1
                          Nco 1
```

```
Gly Ala Arg Cys Glu His Ala Asp Leu Leu Ala Val Val Ala Ala Ser Gln Lys Lys Gln Ala Ile Thr Ala Leu Val Val Val Ser Ile
GGT GCA CGC TGT GAG CAT GCA GAT CTG CTG GCC GTC GTG GCT GCC AGC CAG AAG AAG CAG GCC ATC ACC GCC TTG GTG GTG GTC TTC ATC
                              80              300
                                                                     120                            130                   350
```

```
Val Ala Leu Ala Val Leu Ile Ile Thr Cys Val Leu Ile His Cys Cys Gln Val Arg Lys His Cys Glu Trp Cys Arg Ala Leu Ile Cys
GTG GCC CTG GCT GTC CTT ATC ATC ACA TGT GTC CTG ATA CAC TGC TGC CAG GTC CGA AAA CAC TGT GAG TGG TGC CGG GCC CTC ATC TGC
    110                                               400
```

```
Arg His Glu Lys Pro Ser Ala Leu Leu Lys Gly Arg Thr Ala Cys Cys His Ser Glu Thr Val Val OP
CGG CAC GAG AAG CCC AGC GCC CTC CTG AAG GGA AGA ACC GCT TGC TGC CAC TCA GAA ACA GTG GTC TGA AGAGCCCCAGGAGGAGTTGGCCAGG
       140                                    150                                    160
450                                                                     500                     600                     650
                                                                        Nco 1
```

```
TGGACTGTGGCAGATCAATAAAGAAAGGCTTCTTCAGGACACTGCGGCTTGGGGTTATTC.GTGTCACCTAGAGAAGAAGAAATCAGCGGACCACGATTTCAAGACTTGTTAAAAAAGAACTGCAAAGAGACGGACTCCTGT
 550                              600                                   700                         650                                     750
```

```
TCAAAACTCTCAAGAACTCCGTCGGCTTGGGTTATTC.GTGTCACCTAGAGAAGAAGAAATCAGCGGACCACGATTTCAAGACTTGTTAAAAAAGAACTGCAAAGAGACGGACTCCTGT
                   700                                                 ↑
                                                                       Nco 1
                                                                       850
```

```
TCACCTAGGTGAGGTGTGTGCAGCAGTGGTGTCTGAGTCLACATGTGTGCAGTTGTTCTGCCAGCCATGGATTCCAGGCCSTCCCCCCCCCCCCCCC
                     800
```

HUMAN TRANSFORMING GROWTH FACTOR

CROSS-REFERENCE TO RELATED APPLICATION

This application is a continuation in part of U.S. Ser. No. 06/581,743 now abandoned filed Feb. 17, 1984.

FIELD OF THE INVENTION

The present invention relates to human precursor transforming growth factor-α and its fragments, notably mature human transforming growth factor-α (TGF-α), corresponding to that found in human tissues and to novel forms and compositions thereof and methods for production to homogeneity in therapeutically and/or diagnostically significant quantities.

The present invention enables the production of sufficient quantities of high purity material in comparison to the isolation methods previously employed involving production and extraction from existing cell cultures, which naturally include undesired proteins and which are only available in extremely small quantities.

The publications and other materials cited herein are incorporated herein by reference and, for convenience, generally are numerically referenced in the following text and respectively grouped in the appended bibliography.

BACKGROUND OF THE INVENTION

Transforming growth factors (TGFs) are factors which can elicit a phenotypical transformation of normal cells in a reversible way. It has been shown that administration of TGFs apparently stimulates normal cells to undergo uncontrolled growth of the cells and promotes anchorage independence as measured by formation of transformed cell colonies in soft agar (1–3). Two classes of TGFs have been distinguished. TGF-α is secreted by a wide variety of tumor cells from human or rodent origin (4–7). TGF-α and epidermal growth factor (EGF) are reported to compete for the same receptor (5, 8, 9), which is phosphorylated at tyrosine residues after the binding of TGF-α or EGF (10–11). Some evidence has been presented for the presence of another receptor, specific for TGF-α (12). The anchorage independent growth triggered by TGF-α is strongly potentiated by TGF-β (13, 14). This latter TGF has been detected in many normal and tumor cells (13–17) and has been purified from kidneys (18), placenta (19) and platelets (20). TGF-β is not believed to bind to the EGF receptor and is believed to require EGF or TGF-α for its transforming activity or NRK cells (13–17).

The biological role of the TGFs has not been clearly elucidated. Many studies suggest that TGFs may play an important role in the transformation event. It has been shown that cellular transformation with retroviruses (21–24), SV40 (25) or polyoma virus (26) results in the secretion of TGF-α. The tight linkage of TGF secretion to cellular transformation has been indicated by transfection experiments with polyoma virus DNA, which show that introduction of the DNA segment for middle T antigen is needed and sufficient to trigger both the transformed phenotype and the TGF secretion (26). Transformation studies with a temperature-sensitive mutant of Kirsten murine sarcoma virus also indicate that TGF-α is secreted only when phenotypic transformation occurs at the permissive temperature (21). In addition, recent studies indicate that introduction of the cloned T24 bladder oncogene induces TGF production (27). The biological relevance in tumor development is also suggested by the presence of activity identified as that of TGF-α in the urine of cancer patients, in contrast to the normal controls (28–30). The assay used, however, would not distinguish the activity of other growth factors such as EGF. These and other observations suggest that TGF-α may play a role in tumor formation via an autocrine mechanism, by which the TGFs are secreted by the transformed cells and maintain and stimulate this transformed character of the same cell population (31–32). However, the potentiating effect of TGF-β may be needed as suggested by the secretion of both TGF-α and -β by tumor cells (14). In this way, TGF-α may be a very potent effector molecule during malignant transformation.

Heterogeneous molecular weights for TGF-α are reported for extracts and supernatants from tumor cells (5, 12, 22, 33–34) and in urine (28–30). A small species of about 7 kilodaltons has been purified from both rodent (27, 35) and human (34, 35) cell sources. Amino acid sequence analysis of this rat and mouse TGF-α shows some homology with EGF (27, 35). The reported partial polypeptide sequence of the human TGF-α shows a strong homology with the rat and murine species (35).

It has been observed that patients with metastasized renal cell carcinoma can develop a progressive decalcification of the bone, which is reflected in a humoral hypercalcemia (36). A recent study using impure protein preparations suggests that transforming growth factors (including TGF-α) may cause bone resorption in a tissue culture system (37).

TGF-α can only be produced in such limited quantity by virus transformation of cells as to be impractical for aforementioned use as a therapeutic or diagnostic reagent.

RECOMBINANT DNA TECHNOLOGY

Heterologous proteins, i.e., proteins not normally produced by a cell, are synthesized by cells that have been transformed by exogenous DNA. This typically is accomplished by introducing foreign DNA into a cell in the form of a vector. DNA recombination of the elements of a vector, i.e., an origin of replication, one or more phenotypic selection characteristics, an expression promoter, heterologous gene insert and remainder of the vector, generally is performed outside the host cell. The resulting recombinant replicable expression vehicle, or plasmid, is introduced into cells by transformation and large quantities of the recominant vehicle obtained by growing the transformant. Where the gene is properly inserted with reference to portions which govern the transcription and translation of the encoded DNA message, the resulting expression vehicle is useful to actually produce the polypeptide sequence for which the inserted gene codes, a process referred to as expression. The resulting product may be obtained from intracellular locations by lysing the host cell, or from culture media in the case of secreted products and thereafter recovered by appropriate purification from contaminant proteins.

SUMMARY OF THE INVENTION

The present invention is based upon the discovery that recombinant DNA technology can be used successfully to produce the transforming growth factor-α (TGF-α) precursor and its fragments in amounts sufficient to initiate and conduct animal and clinical testing as prerequisites to market approval. TGF-α precursor and its fragments, including particularly mature TGF-α, and optionally in combination with human transforming growth factor-β, has utility for example in the therapeutic treatment of human beings for bone diseases and to accelerate wound healing. In addition, TGF-α is useful as an adjuvant for cell culture so as to reduce requirements for serum in the culture media (thereby resulting in purification advantages), and to stimulate or enhance cell growth in cell culture. Also, preparation of large quantities of the TGF-α precursor and its fragments enables the preparation of reagents for the assay of the TGF-α precursor and its fragments in body fluids for the diagnosis of neoplastic or other diseases.

The complete nucleotide and imputed amino acid sequence for the TGF-α precursor is depicted in FIG. 3. For convenience in identifying the various principal domains of the precursor we have designated three polypeptides, mature TGF-α (depicted as the boxed sequence in FIG. 3 at residues 40-89), the TGF-α C-terminal polypeptide at residues 90-160 (principally the 62 residue polypeptide from Gln 98 to Val 160), designated herein as TGF-αC, and the TGF-α N-terminal polypeptide from Met 1 to Ala 22 (TGF-αN). As such therefore, the TGF-α precursor is a TGF-α bearing polypeptide including mature TGF-α and is in effect a fusion of TGF-α with its normal flanking sequences. Also, for convenience, the TGF-α precursor and its fragments (including mature TGF-α, TGF-αC and TGF-αN) collectively will be referred to herein as PRTGF-α species. The term TGF-α shall mean mature TGF-α. Also, unless otherwise stated the term PRTGF-α species shall be deemed to include PRTGF-α species derivatives such as amino acid sequence mutants as are more fully described infra. Another PRTGF-α species fragment included herein is composed of TGF-αC and mature TGF-α. This polypeptide, designated TGF-αmC and extending from residues 20-160, is believed to be the an early product of precursor TGF-α expression in mammalian cells since the TGF-αN sequence is believed to function as a signal which would be cleaved from TGF-αmC upon processing by the endoplasmic reticulum. These principal domains may not be found in vivo with precisely the designated amino or carboxyl termini as some variation in cellulas processing is to be expected.

PRTGF-α fragments generally (a) exhibit some biological activity in common with PRTGF-α, e.g., antibody cross-reactivity or induction of anchorage independence, (b) exhibit substantial homology with some region in PRTGF-α and (c) are at least about 5 amino acid residues long, and are ordinarily about from 10 to 130 residues in length.

The invention provides methods for assaying such heretofore unidentified polypeptide fragments of PRTGF-α as TGF-αN and TGF-αC, and provides methods for assaying same without interference from other peptides encompassing or containing part of these sequences.

Since the present invention now makes the complete amino acid sequence of PRTGF-α species known it is possible for the first time to raise antibodies against predetermined amino acid sequences of PRTGF-α species. Amino acid sequences representing PRTGF-α species fragments (other than TGF-α) are linked in immunogenic conjugates to proteins and then used to immunize animals. Such antibodies are useful in specific immunoassays for PRTGF-α species and in passive immunotherapy.

The present invention further comprises essentially pure PRTGF-α species in which the PRTGF-α species are free of contaminants with which the are ordinarily associated in the non-recombinant cellular environment. Such contaminants are those which are normally present with the TGF-α as found in nature, e.g. in cells, cell exudates or body fluids, and include human serum albumin, gamma globulin, lipoproteins, and growth factors such as epidermal growth factor (EGF). Other proteins from the source from which the PRTGF-α species DNA is obtained may be present in the PRTGF-α species compositions herein, e.g. TGF-β and platlet-derived growth factor (PDGF), but here they will be known and present in predetermined amounts. For example, recombinant cell culture in non-human cells enables the production of human TGF-α which are absolutely free of other human proteins.

The present invention is also directed to replicable DNA expression vehicles harboring DNA encoding PRTGF-α species in expressible form, to microorganism strains or cell cultures transformed with such DNA and to microbial or cell cultures of such transformed strains or cultures, capable of producing PRTGF-α species. Still further, this invention is directed to methods for recombinant fermentative synthesis of PRTGF-α species in said microorganisms and cell cultures.

DNA is provided that encodes PRTGF-α species and which, when expressed in recombinant or transformed culture, yields copious quantities of such PRTGF-α species. This DNA is novel because cDNA obtained by reverse transcription of mRNA from PRTGF-α species synthesizing cells contains no introns and is free of any flanking regions encoding other proteins homologous to the source of the DNA.

Chromosomal DNA encoding PRTGF-α species is obtained by probing genomic DNA libraries with cDNA encoding PRTGF-α species. Chromosomal DNA is obtained free of its normal chromosomal environment and is therefore free of regions flanking the upstream 5' end of the first exon or flanking the 3' downstream end of the last exon which encodes other proteins homologous to the genomic DNA source but will contain introns since the genomic coding sequence for human precursor TGF-α is contained in six distinct exons. Such DNA is useful for transforming mammalian cells to synthesize PRTGF-α species as is further described herein.

The isolated PRTGF-α species DNA is readily modified by substitution, deletion or insertion of nucleotides, thereby resulting in novel DNA sequences encoding PRTGF-α species (in the case of nucleotide substitutions that do not change the encoded amino acid sequence) or its sequence mutants. Modified DNA sequences which do not change the amino acid sequence are useful in enhancing the efficiency of PRTGF-α species expression in chosen host-vector systems, e.g. where a human codon is mutated to a codon preferred by an intended host cell.

These novel DNA sequences or fragments thereof are labelled and used in hybridization assays for genetic material (DNA or mRNA) encoding PRTGF-α species.

In processes for the synthesis of PRTGF-α species, DNA which encodes PRTGF-α species is ligated into a replicable (reproducible) vector, the vector used to transform host cells, the host cells cultured and PRTGF-α species recovered from the culture. The PRTGF-α species which are capable of synthesis herein include the TGF-α precursor, its fragments such as TGF-αC and TGF-α, and derivatives thereof including (a) fusion proteins wherein PRTGF-α species (including mature TGF-α) are linked to heterologous proteins or polypeptides by a peptide bond at the amino and/or carboxyl termial amino acids of the TGF-α, (b) insertional or substitutional mutants of PRTGF-α species wherein one or more amino acid residues are mutated and (c) methionyl or modified methionyl, such as formyl methionyl or other blocked methionyl amino-terminal addition derivatives of the foregoing fusions, fragments or mutants.

Vectors which comprise DNA encoding PRTGF-α species operably ligated to a heterologous secretory leader sequence (usually a signal from a protein homologous to the intended host organism) are used to transform host cells. Host cell processing of the resulting PRTGF-α species fusion results in secretion of the PRTGF-α species without amino-terminal methionyl or blocked methionyl.

Also within the scope of this invention are derivatives of PRTGF-α species other than variations in amino acid sequence. Such derivatives are characterized by covalent or aggregative association with chemical moieties. The derivatives generally fall into three classes: Salts, side chain and terminal residue covalent modifications, and adsorption complexes.

After a PRTGF-α species has accumulated in direct recombinant prokaryotic culture (other than as a fusion with a prokaryotic signal sequence) it is separated from other proteins by virtue either of its physical form as water insoluble refractile bodies or its considerable stability against denaturation. Generally, the insoluble matter in the prokaryotic culture is recovered, refractile bodies (which contain the PRTGF-α species) separated from insoluble cell debris and the refractile bodies solubilized. Optionally, glutathione treatment will follow this step in order to enhance proper refolding of the protein. PRTGF-α species from recombinant eukaryotic cell culture is water soluble and does not require resolubilization; it is purified using conventional methods heretofore employed in isolating PRTGF-α species from natural sources.

Purified PRTGF-α species from recombinant cell culture are combined for therapeutic use with physiologically innocuous stabilizers and excipients and prepared in dosage form as by lyophilization in dosage vials or, preferably storage in aqueous preparations. The latter is feasible because PRTGF-α species are quite stable to thermal denaturation due to the prevalence of disulfide bonds in the molecule. Alternatively, PRTGF-α species are incorporated into a polymer matrix for implantation into or attachment onto surgical sites, e.g. in bandages, thereby effecting a timed-release of the PRTGF-α species in a localized high gradient concentration.

PRTGF-α species-containing compositions are administered to animals, particularly patients requiring accelerated tissue growth, in therapeutically effective doses. Suitable dosages will be apparent to the artisan in the therapeutic context.

BRIEF DESCRIPTION OF THE DRAWINGS

FIG. 1 shows oligonucleotides used as hybridization probes for the detection of the DNA sequence for human precursor TGF-α.

FIG. 2 shows a nucleotide sequence of the 180 bp Sau3A-fragment of plasmid pTGF 15-1, containing the exon coding for the first 33 amino acids of human TGF-α. The deduced amino acid sequence is shown. The sequence in capital letters is part of the TGF-α polypeptide, while the smaller letter type shows the amino acid sequence preceding TGF-α in the precursor. The arrows indicate the acceptor and donor site of intervening sequences as determined by comparison with the cDNA sequence. Some relevant restriction sites are indicated.

FIG. 3 shows the nucleotide sequence and deduced amino acid sequence of the cDNA contained in plasmid pTGF-Cl. The G-C tails flank the cDNA at both sides. Numbers above each line refer to the amino acid position, assuming that the single methionine constitutes the $NH_2$-terminus. The deduced amino acids preceding this methionine are given in lower cases and are back numbered. The amino acid sequence for TGF-α is boxed and bounded at both sides with an Ala-Val rich sequence (overlined residues). Some relevant restriction sites are indicated.

DETAILED DESCRIPTION

Figure 4A:
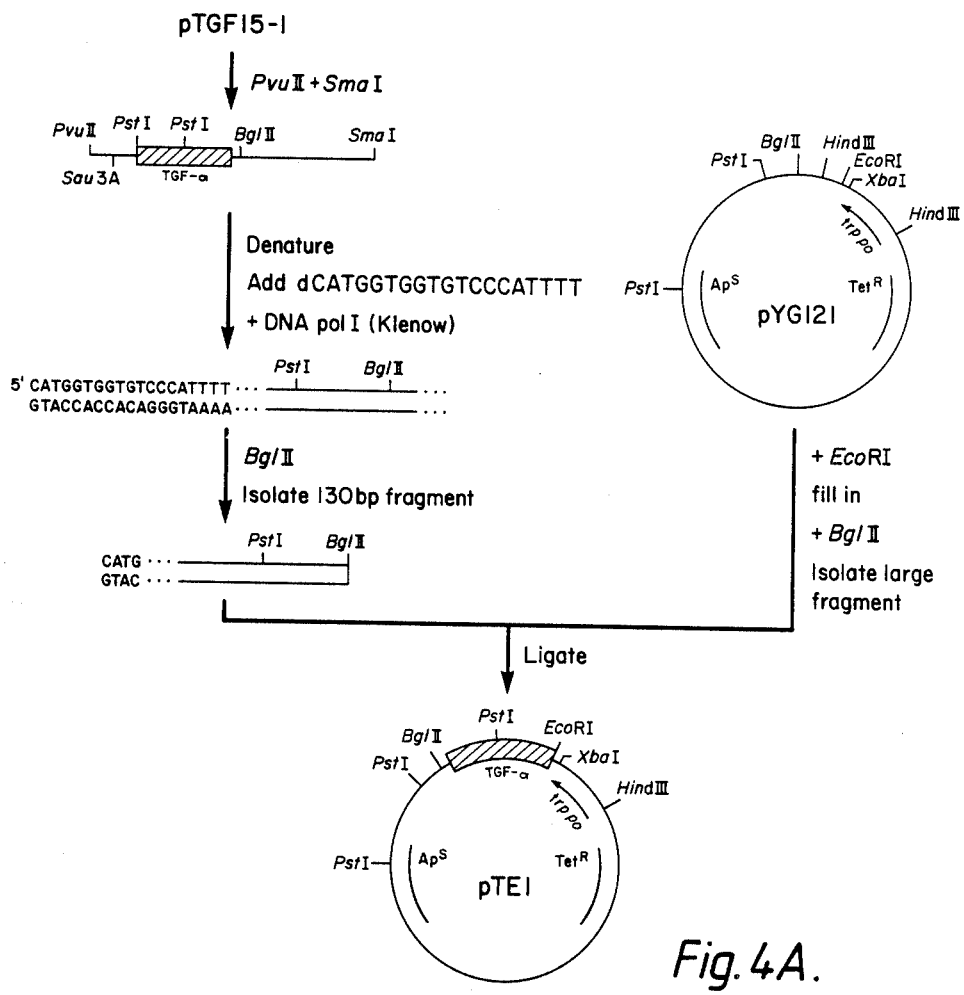
FIG. 4 shows a schematic representation of the construction pathway for plasmids pTE1, 2, 3, 4, 5, 6, 7, 8.
Figure 4B:
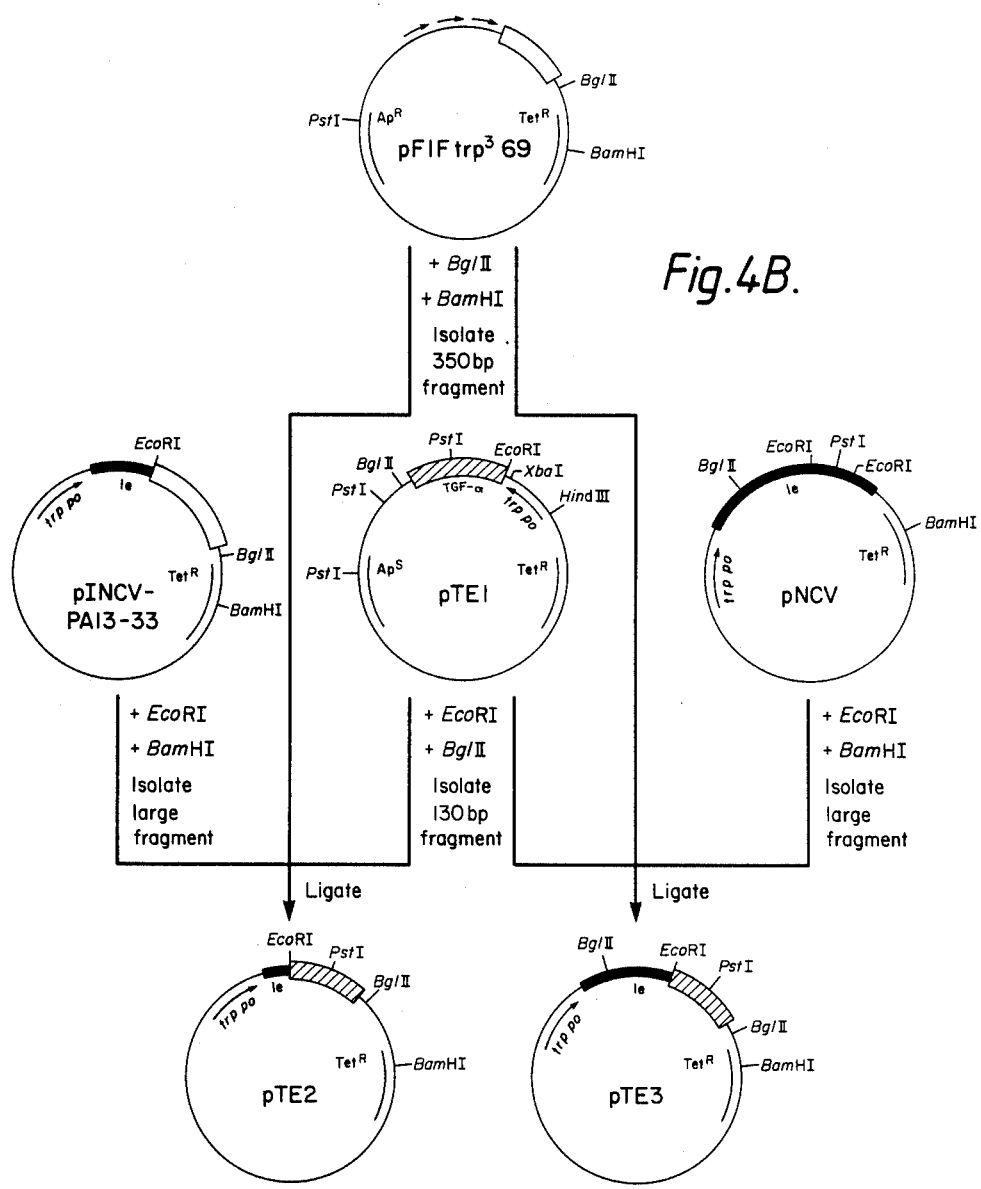
Figure 4C:
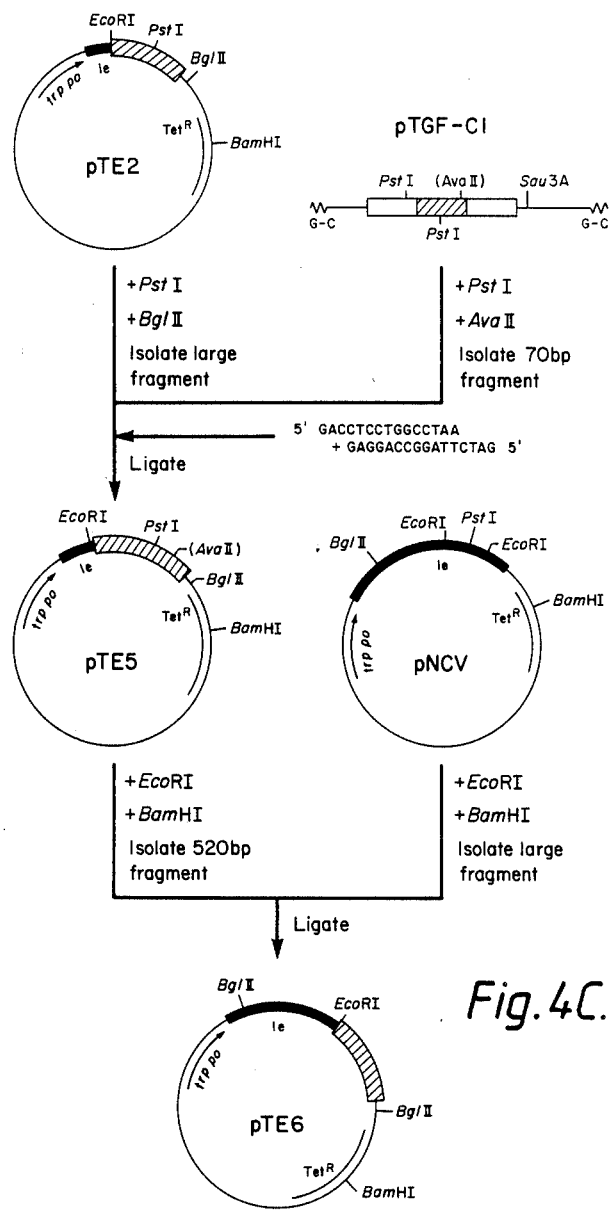
Figure 4D:
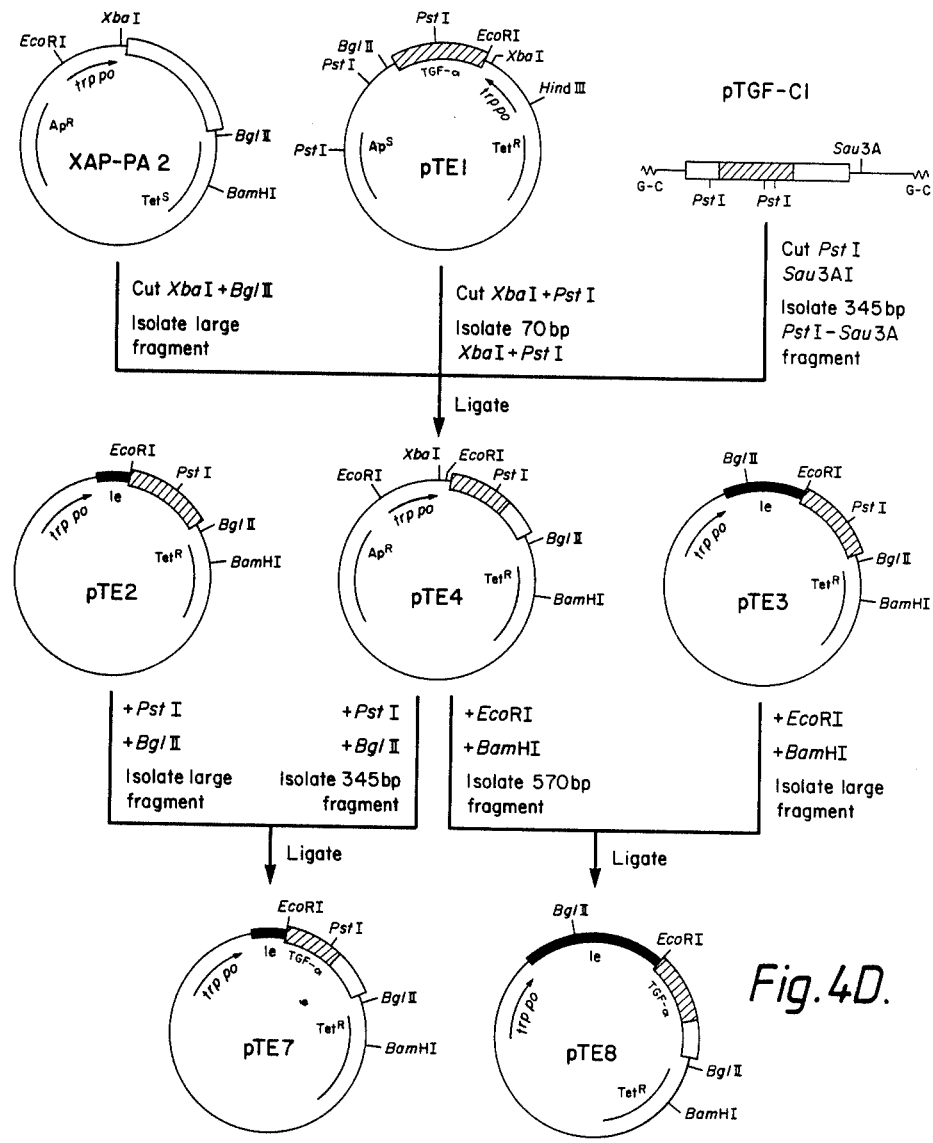

PRTGF-α species are defined for the purposes herein as polypeptides other than EGF which have a substantial region showing functional amino acid homology with the TGF-α precursor amino acid sequence set forth in FIG. 3, or a fragment thereof. A candidate polypeptide is substantially homologous with PRTGF-α species as defined herein if greater than about 35 percent of the residues in the candidate correspond to a sequence within the PRTGF-α species sequence, without making conservative amino acid substitutions or introducing gaps. Ordinarily a candidate polypeptide, in addition to such functional homology, will be capable of exhibiting biological activity in common with its homologous PRTGF-α species.

The degree of amino acid sequence homology which brings a polypeptide within the scope of the definition of PRTGF-α species will vary depending upon whether the homology between the candidate protein and PRTGF-α species falls within or without the PRTGF-α species regions responsible for biological activity: domains which are critical (a) for inducing morphological changes in target cells, (b) for immunological cross-reactivity with antisera raised against PRTGF-α species as may occur in non-recombinant sources, or (c) for cell surface receptor binding should exhibit a high degree of homology in order to fall within the definition, while sequences not involved in maintaining these functions show comparatively low homology. In addition, critical domains may exhibit one or more of these functions and yet remain homologous as defined herein if residues containing functionally similar amio acid side chains are substituted. Functionally similar refers to dominant characteristics of the side chains such as basic, neutral, hydrophobic or acid, or the presence or absence of steric bulk.

Generally a polypeptide defined as PRTGF-α species will contain regions substantially homologous with the FIG. 3 protein or fragments thereof over a continuous domain of at least about from 10 to 25 amino acid residues.

A significant factor in establishing the identity of a polypeptide as a PRTGF-α species is the ability of antisera which are capable of substantially binding to the nonrecombinant counterpart to also bind to the polypeptide in question. However it will be recognized that immunological identity and identity as to other biological activity is not necessarily coextensive. For example, a neutralizing antibody for the receptor binding activity of the mature TGF-α of FIG. 3 may not bind a candidate protein because the neutralizing antibody happens to not be directed to specifically bind a site on mature TGF-α that is critical to its activity. Instead, the antibody may bind an innocous region and exert its neutralizing effect by steric hinderance. Therefore a candidate protein mutated in this innocuous region might no longer bind the neutralizing antibody, but it would nonetheless fall within the definition of TGF-α in terms of its substantial homology with TGF-α.

The language "capable" of biological activity means polypeptides which can be converted, as by enzymatic hydrolysis, from an inactive state anologous to a zymogen to a polypeptide fragment which exhibits the desired biological activity. Typically, inactive precursors will be fusion proteins in which PRTGF-α species is linked by a peptide bond at either terminus to a heterologous protein or fragment thereof. The sequence at this peptide bond is selected so as to be susceptible upon proteolytic hydrolysis to release PRTGF-α species, either in vivo or as part of a manufacturing protocol, in vitro.

While PRTGF-α species ordinarily means human PRTGF-α species, PRTGF-α species from sources such as murine, porcine, equine or bovine are included within the definition of PRTGF-α species so long as they otherwise meet the standards described above for homologous regions. Mature TGF-α in all cases, however, is human TGF-α.

Derivatives of PRTGF-α species factor are included within the scope of the term. Derivatives include amino acid sequence mutants, glycosylated variants and covalent or aggregative conjugates with other chemical moieties. Covalent derivatives are prepared by linkage of functionalities to groups which are found in the PRTGF-α species amino acid side chains or at the N- or C-termini, by means known in the art. These derivatives may, for example, include: Aliphatic esters or amides of the carboxyl terminus or residues containing carboxyl side chains, e.g., asp32 or 49; O-acyl derivatives of hydroxyl group-containing residues such as ser31, ser3, ser42, ser156 or ser94; and N-acyl derivatives of the amino terminal amino acid or amino-group containing residues, e.g. lysine or arginine. The acyl group is selected from the group of alkyl-moieties (including C3 to C10 normal alkyl), thereby forming alkanoyl species, and carbocyclic or heterocyclic compounds which forming aroyl species. The reactive groups preferably are difunctional compounds known per se for use in cross-linking proteins to insoluble matrices through reactive side groups.

Covalent or aggregative derivatives are useful as reagents in immunoassay or for affinity purification procedures. For example, PRTGF-α species are insolubilized by covalent bonding to cyanogen bromide-activated Sepharose by methods known per se or adsorbed to polyolefin surfaces (with or without glutaraldehyde cross-linking) for use in the assay or purification of anti-PRTGF-α species antibodies or cell surface receptors. PRTGF-α species also are labelled with a detectable group, e.g., radioiodinated by the chloramine T procedure, covalently bound to rare earth chelates or conjugated to another fluorescent moiety for use in diagnostic assays, especially for diagnosic of PRTGF-α species levels in biological samples by competitive-type immunoassays.

TGF-αN and TGF-αC are useful as immunogens (alone or as an immunogenic conjugate with a heterologous protein) for raising antibodies against the portions of the TGF-α precursor. In a two-site sandwich specific receptor binding assay, the purpose of which is to distinguish the TGF-α precursor from mature TGF-α, TGF-αN and TGF-αC, anti-αN antibody is immobilized prior to or during the course of the assay procedure, a test sample is incubated with the antibody in order to permit the precursor to bind thereto, and then anti-TGF-αC is incubated with the bound precursor. The anti-TGF-αC is labelled before incubation, for example by radioiodination, or afterwards, for example by incubation with labelled IgG directed against the IgG of the species in which the anti-TGF-αC was raised.

Antisera are raised against the predetermined PRTGF-α species fragments by crosslinking them to immunogenic proteins such as keyhole limpet hemocyanin (KLH) or serum albumin by the use of covalent agents such as glutaraldehyde or succinate anhydride immunizing suitable animals such as mice or rabbits by subcutaneous injection with conventional adjuvants, boosting as necessary and recovering antisera. Monoclonal antibodies are prepared from spleen cells of immunized mice in conventional fashion, e.g. immortalization with EB virus or by cell fusion.

In a method for determination of TGF-αC or TGF-αN without interference from mature TGF-α, antisera are raised against predetermined fragments at opposite ends of the TGF-αC or TGF-αN molecules and the resulting two antisera are employed in a sandwich assay as described above for the assay of the TGF-α precursor. In the case of TGF-αC, for example, the sequence $(Cys)_a$ Arg His Glu Lys Pro Ser Ala Leu Leu Lys Gly Arg Thr Ala (Cys)Hd b, wherein a or b, but not both, is 1, is conjugated to KLH by disulfide bonds and rabbits immunized with the conjugate. The antisera are harvested and stored. Similarly, rabbits are immunized against the TGF-αC sequence His Cys Glu Trp Cys Arg Ala Leu Ile Cys Arg linked to KLH by the use of succinic anhydride at pH6. These two antisera are useful in competitive or sandwich immunoassays. Alternatively, rabbits may be immunized against the entire TGF-αN or TGF-αC polypeptides and two antisera for assay of each polypeptide selected based on their ability to not competitively inhibit one another for binding to TGF-αN or TGF-αC as the case may be. Competitively inhibiting antisera are still useful in competitive-type assays for proteins encompassing the fragment against which antisera were raised, but one will be unable to readily distinguish such other proteins from the fragment. TGF-αmC most conveniently is assayed in body fluid samples such as urine by a sequential or simultaneous sandwich immunoassay in which one of the TGF-αC antibodies is used in concert with an anti-mature TGF-α antibody.

It will be understood that natural allelic variations in PRTGF-α species exist and occur from individual to individual. These variations may be demonstrated by one or more amino acid deletions, substitutions or insertions. Other mutants are predetermined variations in the PRTGF-α species sequence made by site directed mutagenesis of the PRTGF-α species DNA.

The objective of site directed mutagenesis is to construct DNA that encodes PRTGF-α species as defined, but which species also exhibit improved properties and activity. Mutant PRTGF-α species are defined as a polypeptide otherwise falling within the homology definition for PRTGF-α species set forth herein but which have an amino acid sequence different from that of PRTGF-α species whether by way of deletion, substitution or insertion. For example, the lysine residue at position 96 or 97 may be mutated to histidine or another amino acid residue which no longer permits the protein to be proteolytically cleaved at this site. Similarly, cysteine 47, 55, 60, 71, 73 and/or 82 could be replaced by serine, or the carboxyl and/or amino terminus of PRTGF-α deleted. It is not necessary that mutants have all of the biological characteristics of PRTGF-α species where the mutants retain at least one epitopic site which is cross-reactive with antibody to PRTGF-α species.

While the mutation site is predetermined in the PRTGF-α species mutations of this invention it is not necessary that the mutation per se be predetermined. For example, in order to optimize the performance of the position 47, 55, 60, 71, 73 or 82 mutants random mutagenesis may be conducted at the cysteine codons and the expressed PRTGF-α species mutants screened for the optimal combination of biological activity and compatibility with intracellular conditions in prokaryotes, i.e., solubility upon direct expression. Techniques for making substitution mutations at predetermined sites in DNA having a known sequence are well known, for example M13 primer mutagenesis, but here the small size of PRTGF-α species facilitates chemical synthesis of the desired DNA having predetermined mutations.

Mutagenesis is conducted by making amino acid insertions, usually on the order of about from 1 to 10 amino acid residues, or deletions of about from 1 to 30 residues. Substitutions, deletions, insertions or any subcombination may be combined to arrive at a final construct. Insertions include amino or carboxyl-terminal fusions, e.g. a hydrophobic extension added to the C- or N-terminus of mature TGF-α. Obviously, the mutations in the encoding DNA must not place the sequence out of reading frame and preferably will not create complementary regions that could produce secondary mRNA structure.

Not all mutations in the DNA which encode PRTGF-α species will be part of the final product. For example, a major class of DNA insertional mutations are those in which a heterologous secretory leader, or signal, has been appended to the N-terminus of the PRTGF-α species. Alternatively, N-terminal PRTGF-α species fusions with non-secretory heterologous polypeptides are contemplated by this invention where such polypeptides can be cleaved, for example by cyanogen bromide or enzymes, from the PRTGF-α species in order to yield unmethionylated PRTGF-α species. For example, in constructing a procaryotic expression vector the *E. coli* alkaline phosphatase or heat stable enterotoxin II leaders are placed 5' from the PRTGF-α species sequence in reading frame therewith. Yeast invertase, alpha factor or acid phosphatase leaders are similarly used in yeast expression of unmethionylated PRTGF-α species. However, the native TGF-α precursor secretory leader may be recognized by hosts other than cells of its origin, most likely in cell culture of higher eukaryotic cells. When the secretory leader is "recognized" by the host, the fusion protein consisting of PRTGF-α species and the leader ordinarily is cleaved at the peptide bond joining PRTGF-α species and the signal in the events that lead to secretion of the PRTGF-α species. Thus, even though a mutant PRTGF-α species DNA is used to transform the host, and mutant prePRTGF-α species (a fusion) is synthesized as an intermediate, the resulting PRTGF-α species is not a fusion.

As used herein, transforming growth factor-β (TGF-β) denotes transforming growth factor of the β-type with the phenotype of naturally occurring TGF-β, e.g. capable of potentiating TGF-β or EGF (epidermal growth factor) for anchorage independent growth.

DNA encoding PRTGF-α species is covalently labelled with a detectable substance such as a fluorescent group, a radioactive atom or a chemiluminescent group by methods known per se. It is then used in conventional hybridization assays. Such assays are employed in identifying PRTGF-α species vectors and transformants as described in the Examples infra, or for in vitro diagnosis such as detection of PRTGF-α species mRNA in tumor cells.

The mRNA for PRTGF-α species, surprisingly, is relatively rare. This makes the cDNA easy to overlook were one not apprised as to what to look for. However, once its presence is appreciated and completely complementary DNA made available, as is enabled by the disclosures herein, it is routine to screen cDNA libraries of tumor cells for PRTGF-α species cDNA using probes having complementary sequences.

PRTGF-α species are synthesized by host cells, transformed with expression vectors containing DNA which encodes PRTGF-α species. Expression vectors include vectors which together with a host cell are capable of expressing DNA sequences contained therein, where such sequences are operably linked to other sequences capable of effecting their expression. These vectors must be replicable in the host organisms either as episomes or as an integral part of the chromosomal DNA. In general, expression vectors will be plasmids, circular doubled stranded DNA loops which, in their vector form, are not bound to the chromosome. In the present specification, "plasmid" and "vector" generally are used interchangeably as plasmids are the most commonly used form of vector. However, the invention is intended to include such other forms of expression vectors, e.g. cotransformation vectors and viruses which serve equivalent functions.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Recombinant host cells are cells which have been transformed with the above-described vectors. As defined herein, PRTGF-α species are produced in the amounts achieved by virtue of this transformation, rather than in such lesser amounts, or, more commonly, in such less than detectable amounts, as might be produced by the untransformed host. PRTGF-α species produced by such cells are referred to as recombinant PRTGF-α species.

HOST CELL CULTURES AND VECTORS

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, E. coli K12 strain 294 (ATCC No. 31446) is particularly useful. Other microbial strains which may be used include E. coli strains such as E. coli B, and E. coli X1776 (ATCC No. 31537). These examples are, of course, intended to be illustrative rather than limiting.

Prokaryotes may also be used for expression, although our experience has shown that PRTGF-α species sequences generally are deposited in the prokaryotic cell cytoplasm as insoluble refractile bodies. These are readily recovered and resolubilized. The aforementioned strains, as well as E. coli W3110 (F-λ-, protrophic, ATCC 27325), bacilli such as Bacillus subtilus, and other enterobacteriaceae such as Salmonella typhimurium or Serratia marcescens, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (55). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own protein. Those promoters most commonly used in recombinant DNA construction include the β-lactamase (penicillinase) and lactose promoter systems (53, 72, 92) and a tryptophan (trp) promoter system (67, 93). While these are the most commonly used, other microbial promoters have been discovered and utilized, and details concerning their nucleotide sequences have been published, enabling a skilled worker to ligate them functionally with plasmid vectors (80).

In addition to prokaryotes, eukaryotic microbes, such as yeast cultures, may also be used. Yeast express and secrete mature TGF-α at lower levels than bacteria, but the polypeptide is soluble unlike the direct expression product from E. coli. Saccharomyces cerevisiae, or common baker's yeast is the most commonly used among eukaryotic microorganisms, although a number of other strains are commonly available. For expression in Saccharomyces, the plasmid YRp7, for example, (81, 82, 83) is commonly used. This plasmid already contains the trpl gene which provides a selection marker for a mutant strain of yeast lacking the ability to grow in tryptophan, for example ATCC No. 44076 or PEP4-1 (84). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (85) or other glycolytic enzymes (86, 87), such as enolase, glyceraldehyde-3-phosphoglycerate mutase, pyruvate kinase, triosephosphate isomerase, phosphoglucose isomerase, glucokinase and α-factor. In constructing suitable expression plasmids, the termination sequences associated with these genes are also ligated into the expression vector 3' of the sequence desired to be expressed to provide termination of the mRNA and polyadenylation. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (87). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (75). Examples of such useful host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located in front of the PRTGF-α species sequence to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from Polyoma, Adenovirus 2, and most frequently Simian Virus 40 (SV40). The early and late promoters of SV40 virus are particularly useful because both are obtained easily from the virus as a fragment which also contains the SV40 viral origin or replication (88) incorporated herein by reference. Smaller or larger SV40 fragments may also be used, provided there is included the approximately 250 bp sequence extending from the Hind III site toward the BglI site located in the viral origin or replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the PRTGF-α species DNA. An example of a suitable selectable marker is dihydrofolate reductase (DHFR). In selecting a preferred host mammalian cell for transfection by vectors which comprise DNA sequences encoding both a PRTGF-α species and DHFR, it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Natl. Acad. Sci."(USA) 77:4216. Cotransformation is further described in U.S. Pat. No. 4,399,216; the procedures therein are adapted for use in PRTGF-α species synthesis by substitution of DNA encoding a PRTGF-α species sequence for the genomic or β-globin DNA used in the cited patent using appropriate synthetic linkers as required.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of adsorbing MTX appear to be methotrexate sensitive. One such useful cell line is a CHO line, CHO-K1 (ATCC No. CCL 61).

The method by which PRTGF-α species are recovered from cell culture will depend upon whether or not they are expressed as a soluble protein or a refractile body (insoluble aggregate). The latter will usually be the case with bacterial expression, where purification is readily accomplished because most cell proteins are soluble.

Soluble PRTGF-α species are more readily recoverable from cell culture if expressed in a secretory host vector system, e.g. if linked to a bacterial or yeast secretory leader, or if a vertebrate cell line is transformed with the entire TGF-α precursor sequence including its normal signal sequence.

Soluble PRTGF-α species may be purified using alkyl-sepharose chromatography, gel sieving, gel electrophoresis, or receptor-binging affinity chromatography using immobilized antibodies, or receptors.

Compositions containing PRTGF-α species are prepared for administration to patients by mixing PRTGF-α species having the desired degree of purity with physiologically acceptable carriers, i.e., carriers which are nontoxic to recipients at the dosages and concentrations employed. Ordinarily, this will entail combining the PRTGF-α species with buffers, antioxidants such as ascorbic acid, low molecular weight (less than about 10 residues) polypeptides, proteins, amino acids, carbohydrates including glucose or dextrins, chelating agents such as EDTA, and other stabilizers and excipients.

Also administered to animals are compositions containing PRTGF-α species immunogenic conjugates or PRTGF-α species conjugates and antibodies capable of binding to PRTGF-α species, the former to raise antibodies particularly for use in diagnostic kits, the latter to generate anti-body antisera.

The route of administration of such compositions is in accord with known methods, e.g. intravenous, intraperitoneal, intramuscular or intralesional infusion or injection of sterile therapeutic solutions, or by timed release systems as noted below.

PRTGF-α species compositions may be administered from an implantable timed-release article. Examples of suitable systems include copolymers of L-glutamic acid and gamma ethyl-L-glutamate (U. Sidman et al., 1983, "biopolymers" 22 (1): 547–556), poly (2-hydroxyethyl-methacrylate) (R. Langer et al., 1981, "J. Biomed. Mater. Res." 15: 167–277 and R. Langer, 1982, "Chem. Tech." 12: 98–105) or ethylene vinyl acetate (R. Langer et al., Id.). The article is implanted at surgical sites or over wounds. Alternatively, the compositions may be encapsulated in semipermeable microcapsules or liposomes for injection.

The amount of said compositions that is administered will depend, for example, upon the route of administration, the target disease and the condition of the recipient. Intralesional injections will require less composition on a body weight basis than will intravenous infusion. Accordingly, it will be necessary for the therapist to titer the dosage and modify the route of administration as required to obtain optimal activity as can be determined for example by biopsy of the target tissue or diagnostic assays.

TGF-α is a potent bone resorption agent. Accordingly, it is therapeutically useful for this purpose. It is administered by injection, infusion or timed release and the dose is titered by following the plasma calcium ion levels; to induce bone resorption the dose is titered to generate hypercalcemia. In some patients just the converse is the proper therapeutic approach. These patients are those who suffer from carcinoma and, as the case with some tumors, hypercalcemia attendant the synthesis of PRTGF-α species by the tumor cells. These patients are identified by the presence of above-normal concentrations of TGF-αmC or TGF-α in urine, serum or surgically excised tumor tissue if available. The therapeutic regimen involves administering to such patients a TGF-α neutralizing agent such as anti-TGF-α (or its antigen-specific Fab region) or a TGF-α receptor such as the EGF receptor (or its TGF-α-binding amino terminal extracellular domain). Methods are described above for producing antisera to selected TGF-α domains. The antibodies then are screened for their ability upon injection, infusion or timed release to correct the hypercalcemia of such patients. Alternatively, the antibody is generated in situ by immunizing the patient against TGF-α or a selected domain thereof as described above.

The nucleotide and amino acid sequence for the EGF receptor are known (A. Ullrich et al., May 1984, "Nature" 309: 418–425). In addition EGF receptor is obtainable from A431 epidermal carcinoma cells, a publicly available cell line having about 10–50 times more EGF receptor on their surface than most other cell types. A431 cells also secrete a truncated receptor having on the extracellular EGF binding domain (A. Ullrich et al., Id.). Either EGF receptor species is purified according to known methods (M. Waterfield et al., 1982 "J. Cell Biochem." 210: 149–161) or equivalent techniques known to those skilled in the art such as affinity chromatography on EGF linked to cyanogen bromide activated sepharose. They are formulated in pharmaceutically acceptable carriers such as sterile saline in concentrations therapeutically effective upon infusion to bind free TGF-α and thereby lower the serum calcium level. Therapeutic efficacy is monitored by the reduction in hypercalcemia or by assay of free versus bound TGF-α in fashion analogous to immunoassays presently employed for the assay of free thyroxine in plasma. The use of the EGF receptor or the TGF-α receptor (or their TGF-α-binding regions) is preferred over antibodies because of ease of manufacture. However, antibodies have the advantage that they can be selected having affinities greater than those of naturally occuring receptors.

METHODS EMPLOYED

If cells without formidable cell wall barriers are used as host cells, transfection is carried out by the calcium phosphate precipitation method as described in (89). However, other methods for introducing DNA into cells such as by nuclear injection or by protoplast fusion may also be used.

If prokaryotic cells which contain substantial cell wall constructions are used, the preferred method of transfection is calcium treatment using calcium chloride as described by (90).

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments are used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation can be treated for 15 minutes at 15° C. with 10 units of Polymerase I (Klenow), phenolchloroform extracted, and ethanol precipitated.

Size separation of the cleaved fragments is often performed using 6 percent polyacrylamide gel, e.g. as described in Goeddel, et al. (67).

For ligation, the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform E. coli K12 strain 294 (ATCC 31446), and successful transformants selected by ampicillin or tetracyclin resistance where appropriate. Plasmids from the transformants are prepared, analyzed by restriction enzymes and/or sequenced (45, 91).

GENERAL DESCRIPTION OF PREFERRED EMBODIMENTS

Examples

The following examples are intended to illustrate but not to limit the invention. In the examples here an E. coli host culture was employed as host cell culture. However, other eukaryotic and prokaryotic cells are suitable for the method of the invention as well.

1. Isolation of a TGF-α specific genomic DNA clone

Isolation of a TGF-α gene is based upon specific hybridization with synthetic oligonucleotides. These probes were designed on the basis of a preliminary partial amino acid sequence for human TGF-α and are shown in FIG. 1.

It has recently been shown that specific DNA sequences can be isolated from cDNA or genomic DNA libraries by hydridization under low stringency conditions with long synthetic oligonucleotides which contain many mismatches. This approach was successful in the detection of the gene for human insulin-like growth factor I as set forth in U.S. appln. Ser. No. 501,351 filed June 6, 1983 (EPO Application No. 84.3037847), incorporated herein by reference. A similar approach was attempted for the isolation of the DNA sequence coding for human TGF-α. Two long oligonucleotides were synthesized for this purpose (FIG 1). A 41-mer corresponds to a sequence, coding for amino acids 12 to 25, while the 48-mer is complementary to a sequence coding for amino acids 1 to 16. Since several different codons are possible for each amino acid, nucleotide choice of the oligonucleotides was based on the codon bias observed in human mRNAs (94). Also, the presence of multiple CpG dinucleotides was avoided. Since the 3' ends of the 41-mer and the 48-mer are complementary over a length of 15 residues, it is possible to hybridize both oligonucleotides and extend them with avian myeloblastosis virus (AMV) reverse transcriptase, thereby creating a double-stranded 74-mer. In addition to these long oligonucleotides, two sets of 14-mers were synthesized. Four pools of 14-mers, designated 1A, B, C and D are complementary to all possible codons for amino acids 5 to 9. Similarly, four other pools of 14-mers, named 2A through D correspond to amino acids 15 to 19.

These oligonucleotides shown in FIG. 1 were used as hybridization probes for the detection of the DNA sequence for human TGF-α. The oligonucleotides were designed with reference to a partial amino acid sequence for human TGF-α (35) and were synthesized using the solid phase phosphotriester method (38, 39).

The 41-mer, 48-mer and the 14-mers were 5'-labeled with γ-$^{32}$P-ATP and polynucleotide kinase in a reaction mixture containing 70 mM Tris-HCl (pH 7.6),, 10 mM MgCl$_2$, 5 mM dithiothreitol at 37° C. for 30 min. The 74-mer was prepared by heating equimolar amounts of the 41-mer and the 48-mer for 5 min. at 70° C. in a 25 μl mixture of 105 mM Tris-HCl, pH 8.3, 140 mM KCl, 50 mM MgCl$_2$ and 210 mM β-mercaptoethanol and gradually cooling over a 30 min interval to room temperature. These annealed oligonucleotides were subsequently extended to double-stranded radioactively-labeled 74-mers by adding dTTP and dGTP to mM, 150 μCi each of α-$^{32}$P-dATP and α-$^{32}$P-dCTP and 80 units of AMV reverse transcriptase to a total volume of 70 μl. The incubation was for 30 min. at 37° C. Unlabeled dATP and dCTP were then added to 10 mM and the reaction was allowed to proceed for 15 min. The unincorporated nucleotide triphosphates were separated from the hybridization prodes by chromatography over a Sephadex G50 Superfine.

Initially focus was on the isolation of TGF-α specific clones from cDNA libraries derived from mRNA from the human melanoma cell line A2058 (5, 34), which was used as a source for the purification of TGF-α. Extensive screenings with the 14-mers, the 41-mer and the 74-mer permitted the isolation of some hybridizing cDNA clones, which upon sequence analysis were found to be unrelated to TGF-α. Because of this lack of success, it was decided to search for the TGF-α gene in a human genomic DNA library contained in a λ Charon 4A phage (40). About 7.5 × 10$^5$ phages were screened by hybridization with the 41-mer, which was 5'-labeled with $^{32}$P. In another experiment, an equal number of recombinant phages were screened by replica plating of the recombinant λ phages onto nitrocellulose filters (95) and hybridization with the radioactively-labeled 74-mer. These screenings resulted in the detection and isolation of 35 individual recombinant λ phages which hybridized with the 41-mer and/or the 74-mer. DNA was isolated from all 35 phages. Hybridization with the 41-mer, 74-mer, 48-mer and the 14-mer pools 1A–D and 2A–D was assessed by "dot blot" analysis (43) for each recombinant λ DNA. None of these isolated phage DNAs hybridized clearly with the 48-mer or the pools 1A–D, while about half of the DNAs showed some hybridization with a mixture of the 14-mer pools 2A–D.

The 41-mers, 48-mers and 74-mers were hybridized in 5X SSC (1X SSC=0.15M NaCl, 0.015M sodium citrate), 5X Denhardt solution (1X Denhardt solution=0.1 percent Ficoll, 0.1 percent polyvinylpyrollidone, 0.1 percent bovine serum albumin, 20 percent formamide and 50 μg/ml sonicated salmon sperm DNA.

After the filters were prehybridized for 2 hrs at 42° C., the heat denatured probe was added and hybridization took place at 42° C. for 15–20 hrs. The filters were subsequently washed extensively in 1X SSC, 0.1 percent SDS at 37° C. When the 14-mers were used as probes, the prehybridization for 2 hrs and the hybridization for 15 hrs were at 37° C. in 6X SSC, 0.5 percent NP40, 6 mM EDTA, 1X Denhardt solution and 50 μg/ml salmon sperm DNA. Several washes were then performed in 6X SSC at room temperature.

The extent of hybridization with the 41-mer and the 14-mers 2A–D was evaluated by washing the hybridized "dot-blot" nitrocellulose filters under increasingly higher stringency. This was done in order to restrict further the number of phages to be considered as potential candidates for further analysis. Twelve phages were selected for sequence determination on the basis of this evaluation. These phage DNAs were digested with BamHI, HindIII or the combination of both enzymes and the fragments were separated on agarose gel.

Southern analysis (44) of the phage DNAs, which hybridized with the 41-mer or the 14-mer pools 2A–D showed that the sequences hybridizing to either of the probes were localized within a same DNA segment. The hybridizing BamHI or HindIII fragment of each phage DNA was subsequently subcloned into plasmid pBR322. This chimeric plasmids were in turn cleaved with the endonucleases Sau3AI, RsaI, or both. The mixture of fragments was separated on polyacrylamide and agarose gels and transferred onto nitrocellulose filters. Hybridization with the 41-mer permitted the identification of a hybridizing small fragment for all 12 plasmids. These fragments were subsequently subcloned into M13 mp8 or mp9 (45) and their nucleotide sequence was determined by the dideoxynucleotide chain termination method (46).

One of the plasmids, designated pTGF15-1, revealed the sequence coding for the first 33 amino acids of TGF-α, located within a 180 base pair Sau3AI fragment (FIG. 2). pTGF15-1 contains a 10.2 kilobasepair BamHI fragment, derived from the recombinant phage λ15. The codon for the 33rd amino acid is followed by a stop codon. The GT-dinucleotide at that position marks the donor site of an intervening sequence (47). Restriction mapping of pTGF15-1 and further sequence analysis (data not shown) showed that the Sau3AI fragment is located on a 670 bp SacI-BalI fragment and that the Sau3AI site downstream of the splice donor site is also the recognition site for BglII enzyme.

The nucleotide sequence of the 180 bp Sau3A-fragment of plasmid pTGF15-1, containing the exon coding for the first 33 amino acids of human TGF-α and the deduced amino acid sequence are shown in FIG 2. The sequence in capital letters is part of the TGF-α polypeptide, while the small letter type shows the amino acid sequence preceding TGF-α in the precursor. The arrows indicate the acceptor and donor site of the intervening sequences as determined by comparison with the cDNA sequence (see below).

Close examination of this nucleotide sequence shows that 33 residues of the hybridizing 41-mer are homologous with the obtained TGF-α DNA sequence. Fourteen homologous bases are in a continuous stretch. It is not clear why the 48-mer did not hybridize significantly since 37 of the 48 residues are homologous. The perfect homology with one of the 14-mers of pool 2D results in a clear, although surprisingly weak, hybridization. The lack of hybridization with the 14-mers 1A–D is due to the presence of a codon for aspartic acid at position 7 in the mature TGF-α, instead of the lysine which was originally predicted. This difference results in the presence of two mismatching residues in these 14-mers.

The isolated 180 bp Sau3AI fragment of pTGF15-1 was subsequently used as a hybridization probe in a dot blot analysis (43) of the previously isolated 35 recombinant phages. Five of the 35 phage DNAs hybridized with this fragment. Southern analysis shows that they all contain the same hybridizing 670 bp SacI-BalI fragment.

2. A TGF-α mRNA of about 5000 nucleotides long

The above described results show that the genomic sequence coding for human TGF-α is interrupted by an intervening sequence. In order to obtain the full size coding sequence, the genomic SacI-BalI fragment containing the TGF-α exon was used to probe cDNA libraries derived from mRNA from the melanoma line A2058. Since these efforts were again unsuccessful, it was decided to search for another cell line as a source of the TGF-α mRNA.

A collection of different mRNAs, extracted from a wide variety of tumor cell lines, was examined by electrophoresis on formaldehyde agarose gels (41) and "Northern" hybridization (42) with the TGF-α specific SacI-BalI fragment (data not shown). All cell lines showed a weakly, probably non-specifically hybridizing band at the position of the 28S ribosomal RNA, still present in these oligo dT-cellulose selected mRNA preparations. One cell line 1072 F57, derived from a renal cell carcinoma, showed a clearly stronger hybridization signal at the 28S position, indicating the presence of TGF-α mRNA of about 4800-5000 nucleotides long. The related polypeptide EGF is also encoded by an mRNA of about 4800 nucleotides long (48, 49). The primary translation product of this mRNA is an EGF precursor polypeptide, which is subsequently processed into several peptides, one of which is EGF.

3. Isolation of a cDNA coding for TGF-α

In order to isolate a cDNA containing the complete sequence coding for human TGF-α, RNA was isolated from the above cell line. The polyadenylate mRNA fraction was isolated by absorption to oligo dT-cellulose chromatography (50). cDNA was prepared by conventional methods (51-53), tailed with dC-homopolymers (54) and annealed into the PstI-linearized and dG-tailed pBR322 (55). Transformation (56) in $E.$ $coli$ 294 (57) was performed using the high efficiency method of Hanahan (58) and gave rise to three cDNA libraries. One library contained cDNAs which were primed with $dT_{12-18}$, while specifically primed cDNA synthesis from the synthetic 16-mer dCATGCTGGCTTGTCCT was utilized to prepare the two other libraries. This oligonucleotide is complementary to the downstream region (nucleotides 134 to 149) of the TGF-α exon, contained within the 180 bp long Sau3AI restriction fragment of pTGF15-1 (FIG. 2). The bacterial colonies were screened (59) using the radioactively labeled TGF-α specific SacI-BalI restriction fragment prepared from plasmid pTGF15-1. Only one in 90,000 recombinant $E.$ $coli$ clones which are prepared by specifically primed cDNA synthesis, hybridized with the probe. Restriction enzyme analysis of this plasmid, called pTGF-Cl, revealed the presence of three PstI fragments, the shortest of which is the 67 bp fragment also present in the TGF-α exon of pTGF15-1 (FIG. 2). The three pstI fragments, which represent the cDNA insert of about 900 bp, were subsequently subcloned into M13mp8 (45) and sequenced with dideoxy chain termination method (46). The cDNA sequence of plasmid pTGF-Cl with its deduced amino acid sequence is shown in FIG. 3.

FIG. 3 shows the nucleotide sequence and deduced amino acid sequence of the cDNA contained in plasmid pTGF-Cl. The G-C tails flank the cDNA at both sides. The nucleotides are numbered beneath each line. Numbers above each line refer to the amino acid position, assuming that the single methionine constitutes the $NH_2$-terminus. The deduced amino acids preceding this methionine are given in lower cases and are back numbered. The amino acid sequence for TGF-α is boxed and bounded at both sides with an Ala-Val rich sequence (overlined residues).

Examination of the nucleotide sequence shows that the cDNA synthesis did not initiate at the RNA sequence specified by the primer (position 134-149 of the TGF-α exon, FIG. 2), but rather downstream of the position corresponding to the specific oglionucleotide. A gene fragment which is immediately downstream of the 3' end of this cDNA was subsequently isolated from a recombinant phage and did not reveal a sequence which resembles the specific primer. It can therefore be assumed that a random cDNA initiation event generated this TGF-α cDNA. It is possible that the secondary structure of the TGF-α mRNA precluded specific hybridization with the oligonucleotide and therefore the specific cDNA initiation. Alignment of the sequences of the cDNA (FIG. 3) and the genomic fragment from pTGF15-1 (FIG. 2) indicates the presence of a splice acceptor and donor site (47) in the genomic DNA. The TGF-α exon contained with the 180 bp SauAI fragment is thus 121 bp long (FIG. 2).

The recognizable amino acid sequence for TGF-α establishes the reading frame in the cDNA sequence. The coding sequence ends at nucleotide 527 with a TGA as stop codon and is followed by part of the 3' untranslated region. The open reading frame continues up to the 5' end of the cDNA. It is thus possible that only a part of the sequence, coding for the TGF-α precursor, is located on this cDNA, especially since the mRNA is about 4800-5000 nucleotides long. It is, however, significant that the ATG codon for the single methionine residue is preceded by an A at the -3 position and is immediately followed by a G residue. These features are characteristic of the initiation codons in most mRNAs of higher eukaryotes (60). In addition, the sequence between positions 8 and 18 is very characteristic for a hydrophobic core (61) of a signal peptide involved in protein secretion from the cells. Comparison with other signal sequences (61-62) suggests that the cleavage by the signal peptidase could occur following the Ala at position 19, Cys at position 20 or the Ala at position 22, if this sequence indeed represents the signal peptide. However, the assignment of this single methionine as the start of the TGF-α precursor implies that the 3' untranslated sequence of the mRNA would probably have an unusually large length of about 4,000 nucleotides.

The cDNA sequence, shown in FIG. 3, reveals the complete DNA sequence for human TGF-α embedded in a larger coding sequence for the precursor protein. Direct amino acid analysis of the rat, mouse and human TGF-α (27, 35) has revealed the Val-Val sequence at the $NH_2$-terminus. Based on the polypeptide length of 50 amino acids and on the sequenced carboxyl terminus of the rate and mouse TGF-α ends with the Leu-Ala residues at positions 88 and 89 (FIG. 3). In order to generate the 50 amino acid long TGF-α, proteolytic cleavage must occur at both the amino- and carboxyl-termini between alanine and valine residues. This Ala- Val dimer at the NH$_2$-terminus, which is located within the sequence Val-Ala-Ala-Ala-Val-Val, is very similar to the Ala-Val-Val-Ala-Ala sequence found at the carboxyl end. A protease with this remarkable specificity and which could thus be responsible for the proteolytic processing of the TGF-α precursor has not yet been described.

The complete sequence coding for TGF-α has now been determined in the cDNA derived from a renal cell carcinoma and in a gene fragment isolated from a genomic library which was derived from a normal fetal liver (40). Both sequences are identical, indicating that there are no coding differences between the TGF-α genes in both sources.

Alternatively, having established the DNA coding sequence for TGF-α (See FIG. 3), the gene can be synthesized using conventional methods, such as those described in references (38, 39).

The deduced amino acid sequence for the precursor of TGFα reveals a very hydrophobic region beginning at 20 amino acids downstream of the carboxyl terminus of 50 amino acid TGFα. These residues 103 to 121 consist almost exclusively of leucines, isoleucines and valines. The sequence from amino acid 118 to the carboxyl terminus of the precursor polypeptide is remarkably rich in cysteines. This sequence of 42 amino acids contains 8 cysteines, 4 of which are clustered in pairs. This cysteine-rich sequence could possibly constitute a biologically active polypeptide. It can as yet only be speculated how this peptide might be cleaved from the precursor molecule. Several polypeptide hormones are synthesized as larger precursors and are usually bounded by pairs of basic amino acids. The Lys-Lys residues at positions 96–97 could possibly be the site of proteolytic cleavage as in the case of preproenkephalin (63–64), the calcitonin precursor (65) and the corticotropin-β-lipotropin precursor (66).

Gel filtration analysis suggests the existence of some larger TGFs-α with estimated molecular weights of 10 to 23 kilodaltons (1, 5, 22, 28, 29, 30, 33, 34). The nature of these larger TGFs-α is unknown. It is possible that several related genes coding for TGFs-α are present in the genome. However, Southern hybridizations (44) of total human genomic DNA with the 180 bp Sau3AI and the 670 bp SacI-BalI fragment of pTGF15-1 did not reveal the presence of multiple genes. Alternatively, the nature of some of these larger TGFs might be explained by different types of post translational processing of the precursor molecules. It is also possible that aggregation of the TGFs-α with some other proteins could result in an apparent larger molecular weight.

4. Expression of TGF-α in *E. coli*

TGF-α is made in minute amounts by many tumor cells. Indeed, only 1.5 μg of the small TGF-α species has been isolated from 136 liters of culture supernatant of the melanoma cell line A2058, which is considered an "overproducer" of TGF-α (34). This very low availability of the TGF-α from cell culture has hampered its biological characterization. In order to facilitate these studies the synthesis of human TGF-α in *E. coli* was pursued.

As the sequence coding for TGF-α is embedded in a precursor, we introduced a start codon in front and a stop codon behind the coding sequence. The start codon is preceded by an EcoRI recognition site and the stop codon is followed by a BglII site, so that the TGF-α sequence becomes available as a portable EcoRI-BglII restriction fragment (FIG. 4).

TGF-α was expressed as part of different fusion proteins in *E. coli* in a way similar to human somotostatin (72), insulin (73) and desacetylthymosin-αl (74). In these latter cases the mature protein can be cleaved from the fusion polypeptide using cyanogen bromide. This chemical treatment results in the specific cleavage behind the methionine residue (72), which was introduced to connect the front part of the fusion protein with the mature polypeptide. Two plasmids were designed so that the TGF-α coding sequence and its preceding methionine codon are linked at the EcoRI site to the sequence for the front part of a trp leader-trp E fusion protein (trp ΔLE 1413, ref. 76). The expression of this fusion protein is under the control of the trp promoter using the trp leader ribosome binding sequence. In the case of the expression plasmid pTE6, the sequence for the first 190 amino acids of this trp ΔLE 1413 fusion protein, including several cysteine residues, is linked in frame with the TGF-α sequence and followed by a stop codon. In plasmid pTE5 the sequence coding for only the first 17 amino acids of this trp LE fusion protein precedes the TGF-α DNA sequence. This stretch of 17 amino acids does not contain any cysteines, so that the presence of this NH$_2$-terminus would probably not affect the disulfide bond formation of the expressed protein (FIG. 5a). In both cases cleavage with cyanogen bromide will release mature TGF-α because of the presence of a methionine codon in front of the TGF-α coding sequence.

FIG. 4 shows a schematic representation of how several plasmids for expression of TGF-α (amino acids 40–89, FIG. 3), with or without its downstream sequence (amino acids 90–160, FIG. 3) were constructed. Restriction mapping indicated that in pTGF15-1, the 180 bp Sau3AI-BglII fragment which carries the TGF-α exon is contained within a 380 bp PvuII-SmaI fragment. This latter fragment was isolated, denatured and renatured in the presence of the synthetic oligonucleotide dCATGGTGGTGTCCCATTTT, which was 5'-labeled using $\gamma^{32}$P-ATP and T4 kinase. *E. coli* DNA polymerase I Klenow fragment was added to the mixture to catalyze the repair synthesis as described (67). Using this primer repair technique the CATG sequence was introduced in front of the coding sequence for TGF-α. The reaction products were then cut with BglII and the 130 bp fragment containing the partial TGF-α sequence was isolated by polyacrylamide gel electrophoresis. Plasmid pYG121, which is essentially identical to the expression plasmid pIFN-β2 (pBoIFN-β2) (77) except that the bovine IFN-β2 DNA sequence is replaced by a short synthetic DNA fragment, was opened at its unique EcoRI site, filled in with *E. coli* DNA polymerase I (Klenow fragment), and cut with BglII. The 130 bp TGF-α fragment was ligated into this vector, thus restoring the EcoRI site. The resulting plasmid is called pTE1.

The 130 bp EcoRI-BglII restriction fragment which contains the sequence coding for the first 33 amino acids was isolated from pTE1 and ligated to the 350 bp BglII-BamHI fragment of pFIFtrp$^3$69 (67), which contains the front part of the tetracycline resistance gene, and to the large vector fragment of the EcoRI and BamHI cut pINCV-PA13-33 (i.e., pINCV (78), containing a plasminogen activator cDNA insert). The resulting plasmid pTE2 contains the sequence for the first 33 amino acids of TGF-α linked via an EcoRI site to the sequence coding for the NH$_2$-terminal 17 amino acids of the aforementioned trp ΔLE 1413 (ref. 76) fusion protein.

The 130 bp RI-BglII fragment containing the TGF-α sequence was also linked to the sequence coding for the first 190 amino acids of the aforementioned trp LE fusion polypeptide. This plasmid, pTE3, was constructed by ligation of the 130 bp RI-BglII fragment of pTE1 to the BglII-Bam fragment of pFIFtrp$^{369}$ and the large EcoRI and BamHI vector fragment of pNCV (51).

The plasmids for the expression of the complete TGF-α sequence as a short fusion was obtained as follows. pTE2 was cut at its unique PstI and BglIII site and the larger fragment was isolated. The cDNA plasmid pTGF-Cl was cleaved with PstI (position 223, FIG. 3) and AvaII (position 301, FIG. 3) and the 78 bp TGF-α specific fragment was isolated. Both fragments were ligated in the presence of the partially complementary oligonucleotides dGACCTCCTGGCCTAA and dGATGTTAGGCCAGGAG. These oligomers introduce a stop behind the TGF-α coding sequence and connect the AvaII site with the BglII site, The resulting plasmid is pTE5. Plasmid pTE6 has the complete coding sequence for the first 190 amino acids of the trp LE fusion. It was made by ligation of the TGF-α specific 520 bp long EcoRI-BamHI fragment into the large EcoRI-BamHI fragment of pNCV (51). The trp promoter controls the synthesis of the TGF-α short and long fusion proteins from plasmids pTE5 and pTE6, and the expression of the Tet$^R$ gene.

For the direct expression of the DNA sequence (FIG. 4d) for TGF-α, with its connecting downstream coding sequence, plasmid XAP-PA2 was cleaved at the unique XbaI and BglII sites and the large vector fragment was isolated. XAP-PA2 is a plasmid essentially similar to pFIF-trp69 (67) except that the IFN-β cDNA sequence is replaced by the cDNA sequence for human tissue plasminogen activator, modified as in plasmid pt-PA trp12 (70), and that the 641 bp AvaI-PvuII fragment downstream of the Tet$^R$ gene was deleted. In addition, the 70 bp XbaI and BglII fragment was isolated containing the start of the TGF-α sequence from pTE1 and the 345 bp PstI-Sau3AI fragment which contains the rest of the coding sequence from pTGF-Cl. The three fragments were ligated. The resulting plasmid, pTE4, contains the coding sequence preceded by a start codon, as an EcoRI-BglII fragment under the control of the trp promoter.

In addition, to the plasmid pTE4 for direct expression, we also envisaged the expression of this coding sequence as a fusion protein with the NH$_2$-terminal part of the trp leader protein. The TGF-α specific PstI-BglII fragment of 350 bp long was therefore isolated from pTE4 and ligated into the large Pst-BglII fragment of plasmid pTE2. The resulting plasmid is called pTE7. Alternatively, the TGF-α sequence containing EcoRI-BamHI fragment of pTE4 was ligated into the large EcoRI-BamHI fragment of pTE3, giving rise to plasmid pTE8. Plasmids pTE7 and pTE8 contain the TGF-α DNA sequence and its downstream coding sequence linked to the first 17 or 190 amino acids, respectively, of the trp LE 1413 fusion protein (ref. 76). The ligation of these sequences is via an EcoRI site which is followed by the ATG codon for methionine. The presence of the methionine in front of the TGF-α sequence makes it possible to cleave the fusion protein specifically behind this residue.

Restriction enzymes were purchased from New England Biolabs or Bethesda Research Laboratories. T4 kinase was from New England Nuclear, T4 DNA ligase was from Bethesda Research Laboratories, and E. coli DNA polymerase I (Klenow fragment) was from New England Nuclear or Boehringer Mannheim. All enzymes were used essentially as recommended by the manufacturers.

T4 kinase reactions were performed in 70 mM Tris-Cl pH 7.6, 10 mM MgCl$_2$ and 5 mM dithiothreitol. Ligations were in 20 mM Tris-Cl, pH 7.6, 50 mM NaCl, 6 mM MgCl$_2$, 10 mM dithiothreitol, 0.5 mM ATP. Restriction digestions were in 6 mM Tris-Hcl, 6 mM MgCl$_2$, 6 mM β-mercaptoethanol, while the "fill-in" reactions using DNA-polymerase I (Klenow fragment) were done in the same buffer supplemented with 20 μM of each of the 4 dNTPs.

Figure 5:
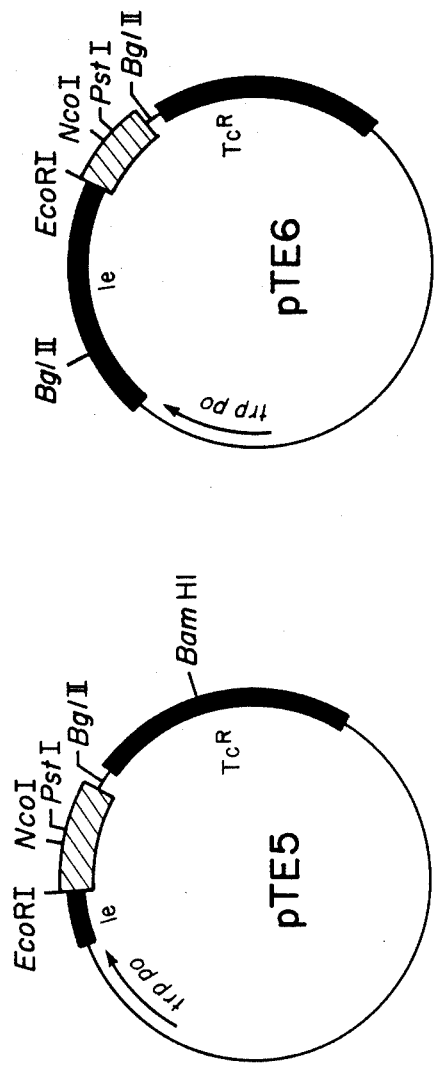
FIG. 5 is a schematic representation of the TGF-α expression plasmids pTE5 and pTE6 indicating the amino acid junction of the TGF-α fusion proteins.

FIG. 5 fives a schematic representation of plasmids pTE5 and pTE6 and shows the amino acid sequence connecting TGF-α with the preceding trp LE fusion protein sequence.

The introduction of these plasmids pTE5 and pTE6 into E. coli W3110 and the subsequent induction of the trp promoter results in the synthesis of high levels of the TGF-α fusion proteins. The long fusion protein, expressed from plasmid pTE6, constitutes the major protein by far in a total bacterial lysate. The short fusion protein encoded by plasmid pTE5 is not synthesized in such high abundance but is nevertheless easily detectable as a prominent band in the E. coli lysate (FIG. 6).

Figure 6:
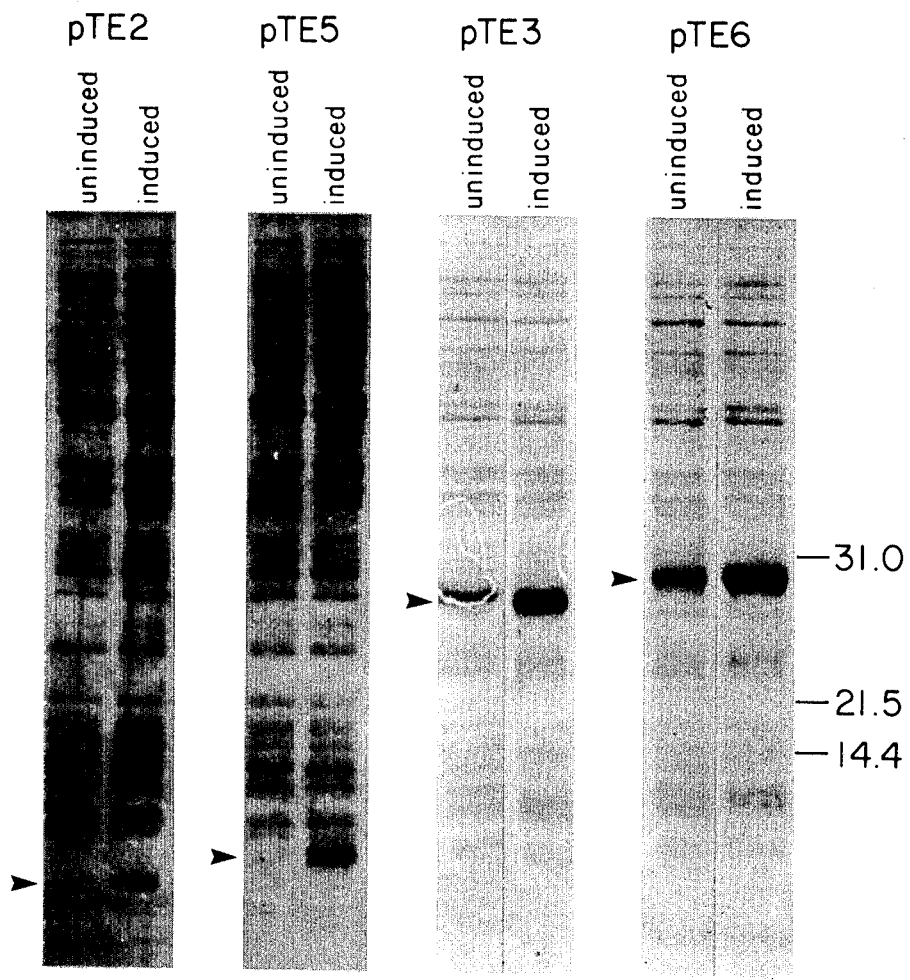
FIG. 6 shows the results upon electrophoresis in a SDS-13 percent polyacrylamide gel (79) of total lysates of E. coli containing the expression plasmids pTE2, pTE3, pTE5, or pTE6. The arrows indicate the TGF-α fusion proteins. The values at the right show the positions of the protein markers.

FIG. 6 shows the results after electrophoresis in a SDS-13 percent polyacrylamide gel (79) of total lysates of E. coli containing the expression plasmids pTE2, pTE3, pTE5 or pTE6. E. coli W3110, transformed with these plasmids was grown at 37° C. in M9 medium containing casamino acids and tetracycline (5 μg/ml) to OD$_{550}$=0.1. Expression from the trp promoter was boosted by adding indolacetic acid to 20 μg/ml. Three ml of bacteria were harvested at OD$_{550}$=0.1 before induction, while a similar number of bacteria were collected at OD$_{550}$=1.0 after induction in the case of pTE2 and pTE5 or OD$_{550}$=0.7 for pTE3 and pTE6. The pelleted bacteria were resuspended in 30 μl 10 mM Tris-HCl pH 7.5, 1 mM EDTA and 3 μl 1 M β-mercaptoethnol and 6 μl 10 percent SDS were added. The mixtures were heated for 2 min at 95° C. and 300 μl cold acetone was added. The acetone precipitate was pelleted, dissolved in 25 μl SDS-loading buffer (5 percent μ-mercaptoethanol, 4 percent SDS, 0.125M Tris-HCl, pH 6.8, 20 percent glycerol) and after heating (2 min. 95° C.) loaded on an SDS-13 percent polyacrylamide gel. The gel was stained with Coomassie Brilliant Blue. Bacterial lysates before and after induction are shown. The arrow marks the TGF-α fusion protein. The position of the molecular weight markers is shown at the right of FIG. 6.

The short TGF-α fusion proteins from E. coli transformed with pTE5 was substantially enriched in order to determine the biological activity. Two procedures, not involving column chromatography, resulted in a purity of 80 to 90 percent. One method is based on the observation that the short TGF-α fusion protein is, in contrast to many other proteins, apparently insoluble in the presence of 0.4M NaCl and 0.5 percent NP40. The precipitate can then be solubilized in 8M urea and dialyzed to 1M acetic acid. The soluble fraction contains mostly the TGF-α fusion protein. Alternatively, the bacteria were sonicated in 70 percent ethanol acidified with HCl, and the TGF-α fusion protein was precipitated from the cleared supernatant by an ether-ethanol precipitation and dissolved in 1M acetic acid essentially as described (18). Gel electrophoretic analysis showed that both procedures resulted in an equally efficient enrichment (FIG. 7).

Figure 7:
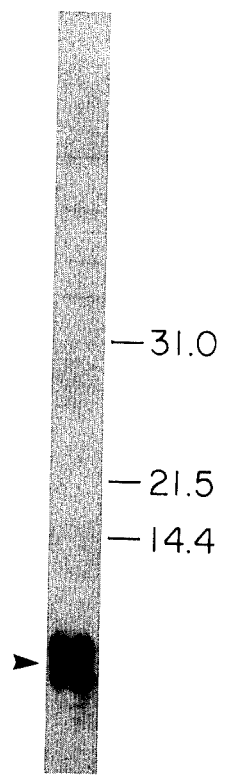
FIG. 7 shows an SDS-polyacrylamide gel of the bacterial short TGF-α fusion protein, enriched by the acid-ethanol method. The 68 residue TGF-α fusion protein migrates as a broad band (arrow) in this gel. The values at the right show the positions of the reference protein markers.

FIG. 7 shows an SDS-polyacrylamide gel (79) of the bacterial short TGF-α fusion protein, enriched by the acid-ethanol method. The 68 amino acid long TGF-α fusion protein migrates as a broad band (arrow) in this gel. The enrichment of the protein by the NP40-NaCl method is very similar.

The bacterial TGF-α short fusion protein thus obtained was tested in two different assays. It has been shown that natural TGF-α competes with EGF for the same receptor (5, 8, 9). This has led to the development of a fast and quantitative binding assay for TGF-α, based on the competition with $^{125}$I-labelled EGF (5, 14, 27). The results from binding experiments using NRK cells (15, 19, 27) indicate unambiguously that the TGF-α short fusion protein, as well as the TGF-α generated by cyanogen bromide cleavage (not shown) from the same fusion protein, bind to the EGF-receptor. However, the binding of the short TGF-α fusion protein is only 0.5–1 percent of the expected value, if one assumes quantitatively equivalent binding of TGF-α and EGF for the same receptor under the experimental conditions. It is possible that the low value may be due to an intrinsically lower binding affinity of human TGF-α, or to the presence of molecules with aberrant configurations or to the use of binding conditions which are not optimal for the bacterial TGF-α.

Figure 8:
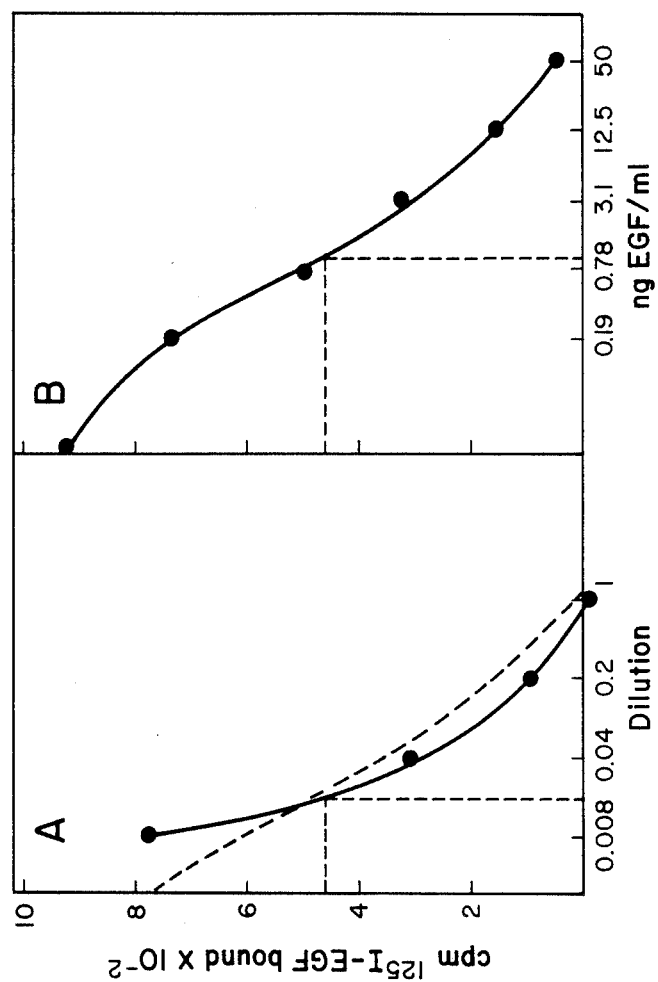
FIG. 8A shows the competition of the bacterial TGF-α short fusion protein with $^{125}I$-labelled EGF in a radioreceptor assay (solid line), performed and graphically represented as described (5, 14, 27). The calibration curve with EGF is shown as a dashed line.
FIG. 8B shows the EGF calibration curve. The ordinate shows the binding of $^{125}I$-labelled EGF to the cells.

The A panel of FIG. 8 shows the competition of the bacterial TGF-α short fusion with $^{125}$I-labelled EGF in a radioreceptor assay (solid line). The calibration curve with EGF is shown as a dashed line. Panel B shows the EGF calibration curve separately.

Figure 9:
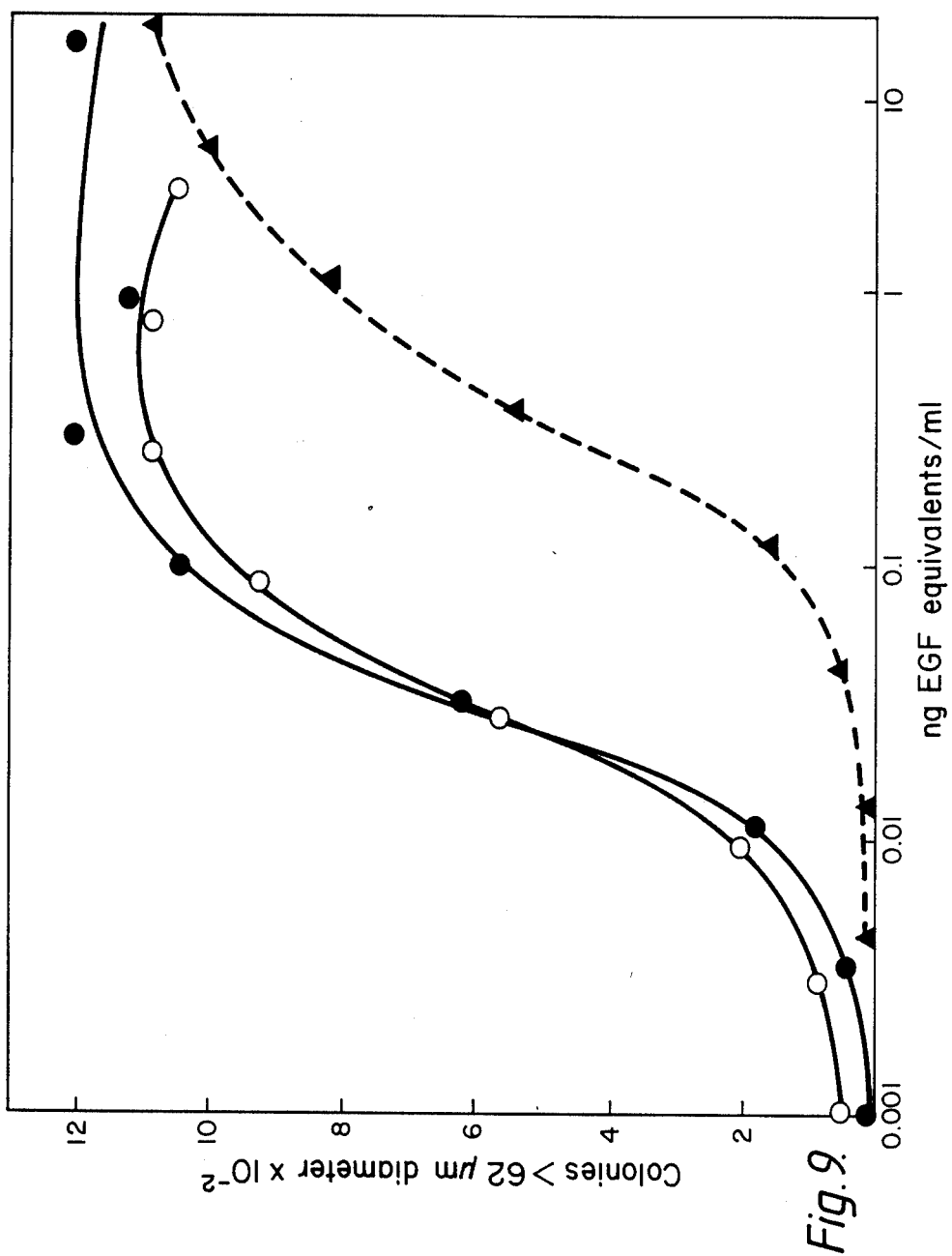
FIG. 9 shows soft-agar colony-forming activity of murine EGF, the bacterial TGF-α fusion protein, before and after cleavage with cyanogen bromide. The assay was performed in the presence of human TGF-β using NRK cells, clone 49F, as described (14). The ordinate scores the number of colonies larger than 850 $\mu m^2$, while the abscissa indicates the concentration of EGF or bacterial TGF-α, expressed in EGF equivalents (ng/ml), as determined in the EGF, while the solid lines give the results for the bacterial TGF-α fusion protein before (open circle) or after (closed circle) treatments with cyanogen bromide.

The biological activity of TGF-α can be measured by its ability to induce anchorage independence of non-transformed cells, such as NRK cells. The presence of TGF-α or EGF induces the formation of colonies. The number and size of these colonies is strongly increased in the presence of TGF-β (13–14). The bacterial TGF-α, purified as indicated before, was tested for the ability to induce anchorage independence, using NRK cells (140). FIG. 9 also shows soft-agar colony-forming activity of murine EGF and the bacterial TGF-α fusion protein before and after cleavage with cyanogen bromide (75). The assay was performed in the presence of TGF-β with NRK cells, clone 49F, as described (14). The ordinate scores the number of colonies larger than 850 μm², while the abscissa indicates the concentrations of EGF or bacterial TGF-α, expressed in EGF equivalents (ng/ml), as determined in the EGF receptor binding assay. The dashed line shows the curve for EGF, while the solid lines give the results for the bacterial TGF-α fusion protein, before (o) or after (o) cleavage with cyanogen bromide. These results clearly show that the TGF-α short fusion triggers colony formation in soft agar in the presence of TGF-β. It is remarkable that in these assays the bacterial TGF-α is about 20 to 30 times more active relative to EGF than it is in the radioreceptor assay. This quantitative difference was also apparent with the cyanogen bromide cleaved TGF-α fusion protein. The number and the size of colonies, induced by the bacterial TGF-α, in the absence of TGF-β, is much smaller than in the presence of TGF-β, but also under these assay conditions the quantitative differences between the bacterial TGF-α and EGF remain unchanged.

The results from both types of assays show that the bacterial TGF-α fusion protein, with its additional 17 NH$_2$-terminal amino acids, and the cyanogen bromide cleaved protein compete with EGF and can induce anchorage independence of NRK cells. The ability to induce colony formation in soft agar is much higher than expected on the basis of the radioreceptor assay. In all cases TGF-α has 20 to 30 fold higher activity in soft agar than it has in the radioreceptor assay (relative to EGF).

Massague et al. (12) have presented evidence that TGF-α binds not only to the EGF receptor but also to a 60 kd TGF-α specific receptor. It is possible that the binding to this latter receptor mediates in part the induction of the anchorage-dependent character by TGF-α. If so, the EGF radioreceptor assay may not be predictive in an absolute manner for the colony formation in soft agar. It could also be possible that the binding characteristics of TGF-α to either of these receptors are not the same. In contradiction to this, Carpenter et al. (8) have recently shown that the induction of anchorage independence by TGF-α can be blocked by the presence of antisera to the EGF receptor, indicating that the binding to this receptor is required for the appearance of colonies in soft agar. It is also possible that the binding of the bacterial TGF-α to the EGF receptor is more efficient under conditions for the soft agar assay than during the radioreceptor assay, and that this may explain the quantitative differences observed between both assays.

5. Expression of TGF-α in Yeast

Figure 10:
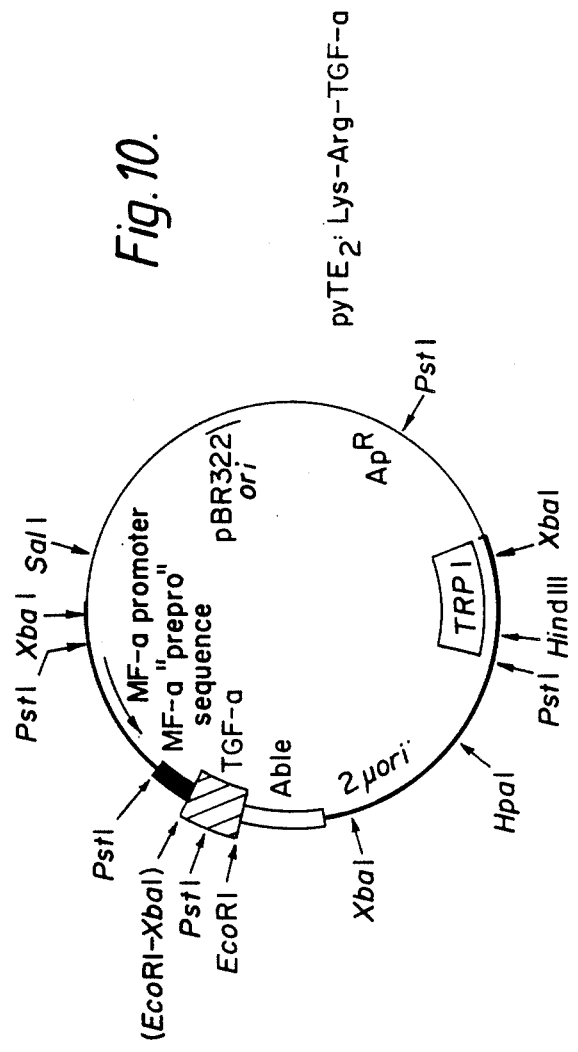
FIG. 10 depicts plasmid pyTE2 for yeast expression of TGF-α. This plasmid has the TGF-α sequence (dashed) with the preceding α-factor (MF-α) prepro sequence under the transcriptional control of the α-factor promotor. The TGF-α sequence is followed by the "Able" gene 3' untranslated region and polyadenylation signal (open box). The TRP1 functions as the selection marker in yeast. The replication in yeast is assured by the presence of the 2μ replication origin. $AP^R$: ampicillin resistance. The junction between the α-factor prepro sequence and the TGF-α sequence is shown at the right of the plasmid map.

A plasmid was designed which was aimed at the expression of TGF-α in yeast and subsequent secretion into the yeast medium. For this purpose we explored the use of the gene coding for the mating factor-α in yeast. This α-factor is secreted from the yeast *S. cerevisiae* and plays an important physiological role in the mating process. The gene for this α-factor has been isolated and codes for a large precursor. The prepro-α-factor polypeptide comprises an amino-terminal signal peptide needed during the secretion process, and 4 identical α-factor peptide units. Release of these α-factor peptides most likely involves a proteolytic cleavage of the precursor at the dibasic Lys-Arg residues, located downstream of the signal peptide and in front of the α-factor units (J. Kurjan et al., 1982, "Cell" 30: 933; Singh et al., 1983, "Nucl. Acids Res." 11: 4049. A TGF-α expression plasid (pyTE2) was constructed in which the sequence coding for the 50 amino acid TGF-α and its flanking stop codon was introduced in frame immediately following the codons for the yeast α-factor Lys-Arg dipeptide. The sequence for the amino terminal part of the prepro-α-factor including the signal peptide is retained. The expression of this TGF-α fusion polypeptide is under the control of the α-factor promoter. Suitable starting plasmids for this and equivalent constructions are described in EP No. 123,544A. Expression plasmid pyTE2 (FIG. 10), also contains a functional yeast replication origin derived from the 2μ plasmid (J. Hartley et al., 1980, "Nature" 286: 860), a transcriptional terminator and polyadenylation site from the "Able" gene (J. Hartley et al., id.) and the TRP-1 selection marker (G. Tschumper et al., 1980 "Gene" 10: 157–166).

*Saccharomyces cerevisiae* strain 20B-112 (E. Jones, 1976, "Genetics" 85: 23) was transformed with pyTE2. The medium of the transformed yeast was assayed both in the radioreceptor assay and in the soft agar colony formation. Using both assays, biologically active TGF-α could be detected in the yeast medium. Further analysis showed that about 8 ng of TGF-α can be recovered per ml of medium and that following the synthesis in yeast more than 90 percent of the biologically active TGF-α is secreted. It is likely that the secreted TGF-α has the proper disulfide bond configuration, since refolding the disulfide bridges is not needed for activity. Using a similar α-factor based expression vector, Brake et al., 1984, "Proc. Natl. Acad. Sci. USA" 81: 4642, have recently been able to express and secrete human EGF from yeast.

6. Expression of a TGF-αC Polypeptide pTE4 was digested with BglI and BamHI and the TGF-αC-containing fragment recovered. An oligonucleotide primer having the sequence

```
                    MetIleIleThrCysValLeu
GATCG*AATTCATGATCATCACATGTGTCTG
      EcoRI
``` was prepared, representing an EcoRI site, a methionine codon and the first six residues of a TGF-αC polypeptide starting at Ile 115 of the precursor. The regions in the TGF-αC-containing fragment which were 5' to this primer were deleted by primer extension following conventional procedures. The DNA encoding the TGF-αC polypeptide was recovered by gel electrophoresis of an EcoRI and BglII digest. Alternatively, this DNA could be prepared by organic synthesis.

pTE5 was digested with EcoRI and BglII, and the large vector fragment recovered. The recovered pTE5 fragment and the EcoRI-BglII TGF-αC fragment from the previous steps were ligated with T4 ligase, the mixture used to transform $E.\ coli$ and the bacteria cultured as described above. TGF-αC was relatively toxic to $E.\ coli$. Better yields might be obtained by modifying the oligonucleotide so that the $E.\ coli$ StII or alkaline phosphatase signals are inserted in place of the ATG start codon, or by expressing the TGF-αC gene in a mammalian cell transformation host-vector system.

BIBLIOGRAPHY

1. De Larco, et al., *Proc. Natl. Scad. Sci. (USA)* 75 (1978).
2. Todaro, G. J., et al., *J. Supramolec. Cell. Biochem.* 15, 287 (1981).
3. Roberts, et al., *Federation Proceedings* 42, 2621 (1983).
4. Roberts, A. B., et al., *Proc. Natl. Acad. Sci. (USA)* 77, 3494 (1980).
5. Todaro, G. J., et al., *Proc. Natl. Acad. Sci. (USA)* 77, 5258 (1980).
6. Ozanne, B., et al., *J. Cell. Physiol.* 105, 163 (1980).
7. Mozes, H. L., et al., *Cancer Res.* 41, 2842 (1981).
8. Carpenter, G., et al., *Proc. Natl. Acad. Sci. (USA)* 80, 5627 (1983).
9. Massague, J., *J. Biol. Chem.* 258, 13614 (1983).
10. Reynolds, F. H. Jr., et al., *Nature* 292, 259 (1981).
11. Pike, L. J., et al., *J. Biol. Chem.* 257, 14628 (1982).
12. Massague, J., *Proc. Natl. Acad. Sci. (USA)* 79, 6822 (1982).
13. Anzano, M. A., et al., *Cancer Res.* 52, 4776 (1982).
14. Anzano, M. A., et al., *Proc. Natl. Acad. Sci. (USA)* 80, 6264 (1983).
15. Roberts, A. B., et al., *Proc. Natl. Acad. Sci. (USA)* 78, 5339 (1981).
16. Roberts, A. B., et al., *Nature* 295, 417 (1982).
17. Anzano, M. A., et al., *Anal. Biochem.* 125, 217 (1982).
18. Roberts, A. B., et al., *Biochemistry*, 22: 5692–5698 (1983).
19. Frolik, C. A., *Proc. Natl. Acad. Sci. (USA)* 80, 3676 (1983).
20. Assoian, R. K., et al., *J. Biol. Chem* 258, 7155 (1983).
21. Ozanne, B., et al., *J. Cell. Physiol.* 105, 163 (1980).
22. Todaro, G. J., et al., *In: Hormones and Cell Culture, Cell Proliferation Conference* 6, Sato, G. H., et al., eds. (Cold Spring Harbor, N.Y.), 113 (1979).
23. Twardzik, D. R., et al., *Science* 216, 894 (1982).
24. Twardzik, D. R., et al., *Virology* 124, 201 (1983).
25. Kaplan, P. L., et al., *Virology* 108, 484 (1981).
26. Kaplan, P. L., et al., *Virology* 123, 327 (1980).
27. Massague, J., *J. Biol. Chem.* 258, 13606 (1983).
28. Sherwin, S. A., et al., *Cancer Research* 43, 403 (1983).
29. Kimball, E. S., et al., *Cancer Research*, 44: 3613–3619 (August 1984).
30. reference deleted.
31. Sporn, M. B., et al., *New Engl. J. Med.* 303, 878 (1980).
32. Kaplan, P. L., et al., *Proc. Natl. Acad. Sci. (USA)* 79, 485 (1982).
33. Todaro, G. J., et al., *Cancer Res.* 38, 4147 (1978).
34. Marquardt, H., et al., *J. Biol. Chem.* 257, 5220 (1982).
35. Marquardt, H., et al., *Proc. Natl. Acad. Sci. (USA)* 80, 4684 (1983).
36. Mundy, G. R.., *Life Sci.* 23, 1735 (1978).
37. Ibbotson, K. J., et al., *Science* 221, 1292 (1983).
38. Crea, R., et al., *Nucl. Acids Res.* 8, 2331 (1980).
39. De Rooij, J. F. M., et al., *Recl. Trav. Chim. Pays-Bas* 98, 537 (1979).
40. Lawn, R. M., et al., *Cell* 15, 1157 (1978).
41. Dobner, P. R., et al., *Proc. Natl. Acad. Sci. (USA)* 78, 2230 (1981).
42. Thomas, P. S., *Proc. Natl. Acad. Sci. (USA)* 77, 5201 (1980).
43. Kafatos, F. C., et al., *Nucl. Acids Res.* 7, 1541 (1979).
44. Southern, E. M., *J. Mol. Biol.* 98, 503 (1975).
45. Messing, J., et al., *Nucleic Acids Res.* 9, 309 (1981).
46. Smith, A. J. H., *Meth. Enzym.* 65, 560 (1980).
47. Breathnach, R., et al., *Ann. Rev. Biochem.* 50, 349 (1981).
48. Gray, A., et al., *Nature* 303, 722 (1983).
49. Scott, J., et al., *Science* 221. 236 (1983).
50. Aviv, H., et al., *Proc. Natl. Acad. Sci. (USA)* 69, 1408 (1972).
51. Goeddel, D. V., et al., *Nature* 287, 411 (1980).
52. Wickens, M. P., et al., *J. Biol. Chem.* 253, 2483 (1978).
53. Goeddel, D. V., et al., *Nature* 281, 544 (1979).
54. Chang, A. C. Y., et al., *Nature* 275, 617 (1979).
55. Bolivar, F., et al., *Gene* 2, 95 (1977).
56. Hershfield, V., et al., *Proc. Natl. Acad. Sci. (USA)* 76, 3455 (1979).
57. Backman, K., et al., *Proc. Natl. Acad. Sci. (USA)* 73, 4174 (1976).
58. Hanahan, D., *J. Mol. Biol.* 166, 557 (1983).
59. Hanahan, D., et al., *Gene* 10, 63 (1980).
60. Kozak, M., *Nucl. Acids Res.* 9, 5233 (1981).
61. Perlman, D., et al., *J. Mol. Biol.* 167, 391 (1983).

62. Blobel, G., et al., *Soc. Exp. Biol. Symp.* 33, 9 (1979).
63. Noda, M., et al., *Nature* 295, 202 (1982).
64. Gubler, U., et al., *Nature* 295, 206 (1982).
65. Amara, S. G., et al., *Nature* 298, 240 (1982).
66. Nakanishi, S., et al., *Nature* 278, 423 (1979).
67. Goeddel, D. V., et al., *Nucl. Acids. Res.* 8, 4057 (1980).
68. Gray, P. W., et al., *Nature* 295, 503 (1982).
69. McGrath, J. P., et al., *Nature* 295, 423 (1982).
70. Pennica, D., et al., *Nature* 301, 214 (1983).
71. Seeburg, P. H., et al., *DNA* 2. 37 (1983).
72. Itakura, K., et al., *Science* 198, 1056 (1977).
73. Goeddel, D. V., et al., *Proc. Natl. Acad. Sci. (USA)* 76, 106 (1979).
74. Wetzel, R., et al., *Biochemistry* 19, 6096 (1980).
75. *Tissue Culture,* Academic Press, Kruse and Patterson, Eds. (1973).
76. Miozzari, G. F. and Yanofsky, C., *J. Bacteriol.* 133, 1457–1466 (1977).
77. European Patent Application Publication No. 0088622.
78. Yansura, D., et al., EPO No. 0068693, fragment 3a.
79. Laemmli, U. K., *Nature* 227, 680 (1970).
80. Siebenlist, et al., *Cell* 20, 269 (1980).
81. Stinchcomb, et al., *Nature* 282, 39 (1979).
82. Kingsman, et al., *Gene* 7, 141 (1979).
83. Tschumper, et al., *Gene* 10, 157 (1980).
84. Jones, *Genetics* 85, 12 (1977).
85. Hitzeman, et al., *J. Biol. Chem.* 255, 2073 (1980).
86. Hess, et al., *J. Adv. Enzyme Reg.* 7, 149 (1968).
87. Holland, et al., *Biochemistry* 17, 4900 (1978).
88. Fiers, et al. *Nature* 273, 113 (1978).
89. Graham, et al., *Virology* 52. 546 (1978).
90. Cohen, et al., *Proc. Natl. Acad. Sci. (USA)* 69, 2110 (1972).
91. Maxam, et al., *Methods in Enzymology* 65, 449 (1980).
92. Chang, et al., *Nature* 275: 615 (1979)
93. EPO Appln. Publ. No. 0036776.
94. Grantham, R., et al., *Nucl. Acids Res.* 9, r43 (1981).
95. Benton, W. D. and Davis, R. W., *Science* 196, 180–182 (1977).

We claim:

1. An expression vector comprising a DNA sequence encoding a human TGF-α species selected from the group of
   (1) precursor TGF-α;
   (2) a biologically active fragment of precursor TGF-α having at least about 50 residues; or
   (3) a biologically active mutant of precursor TGF-α or a fragment of precursor TGF-α having at least about 50 residues, wherein an amino acid residue has been inserted, substituted or deleted in or from the amino acid sequence of the precursor TGF-α sequence or its fragment.

2. The vector of claim 1 wherein the biologically active mutant binds to a cell surface receptor for TGF-α and is an insertional or substitutional mutant of mature TGF-α.

3. The vector of claim 2 wherein the fragment is mature TGF-α.

4. The vector of claim 1 wherein the mutant comprises an insertion of a heterologous polypeptide at carboxyl-terminus and/or amino terminus of mature TGF-α.

5. The vector of claim 3 wherein a methionyl residue is added to the amino terminus of the mature TGF-α.

6. The vector of claim 1 which is a plasmid or virus.

7. A method for producing a TGF-α species, comprising
   (a) preparing an expression vector comprising a DNA sequence encoding a human precursor TGF-α species selected from the group of
      (1) precursor TGF-α;
      (2) a biologically active fragment of precursor TGF-α having at least about 50 residues; or
      (3) a biologically active mutant of precursor TGF-α, or a fragment thereof having at least about 50 residues, wherein an amino acid residue has been inserted, substituted or deleted in or from the amino acid sequence of the precursor TGF-α sequence or its fragment;
   (b) transforming said host cell with the expression vector to obtain a recombinant host cell;
   (c) culturing the recombinant host cell under conditions for expression of the TGF-α species; and
   (d) recovering the TGF-α species from the host cell culture.

8. The method of claim 7 wherein the host cell is yeast.

9. The method of claim 7 wherein the TGF-α species is mature TGF-α.

10. The method of claim 7 wherein the TGF-α species is recovered as insoluble aggregates and thereafter is resolubilized.

11. The method of claim 7 wherein the TGF-α species is secreted from the host cells and is recovered from the host cell culture medium.

* * * * *

UNITED STATES PATENT AND TRADEMARK OFFICE
CERTIFICATE OF CORRECTION

PATENT NO. : 4,742,003

DATED : May 3, 1988

INVENTOR(S) : DERYNCK and GOEDDEL

It is certified that error appears in the above-identified patent and that said Letters Patent is hereby corrected as shown below:

In Col. 30, Claim 3, line 13, change "2" to --1--.

Signed and Sealed this

Sixth Day of December, 1988

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,742,003

DATED : 03 May 1988

INVENTOR(S) : R.M.A. DERYNCK and D.V. GOEDDEL

Page 1 of 5

It is certified that error appears in the above-identified patent and that said Letters Patent is hereby corrected as shown below:     Title Page:

left column, change the filing date from "May 14, 1985" to --February 11, 1985--.

right column, line 3, change "Marguardt" to --Marquardt--.

right column, line 8, change "Marguardt" to --Marquardt--.

right column, line 11, change "Toduro" to --Todaro--.

right column, line 17, change "Surcoma" to --Sarcoma--.

In Figure 1, line 1, change "olignucleotide" to --oligonucleotide--.

In col. 2, line 51, change "recominant" to --recombinant--.

In col. 3, line 5, after "utility" insert a comma and after "example" insert a comma.

In col. 3, line 40, delete "the".

In col. 3, line 46, change "cellulas" to --cellular--.

UNITED STATES PATENT AND TRADEMARK OFFICE
CERTIFICATE OF CORRECTION

PATENT NO. : 4,742,003
DATED : 03 May 1988
INVENTOR(S) : R.M.A. DERYNCK and D.V. GOEDDEL It is certified that error appears in the above-identified patent and that said Letters Patent is hereby corrected as shown below:

In col. 4, line 5, change "the" to --they--.

In col. 4, line 14, change "platlet" to --platelet--.

In col. 4, line 18, change "are" to --is--.

In col. 4, line 67, after "vector" (second occurrence) insert --is--.

In col. 4, line 68, after "cells" (second occurrence) insert --are--.
In col. 5, line 1, after "species" insert --are--.
In col. 5, line 37, after "species)" insert --are--.

In col. 5, line 38, after "bodies" insert --are--.

In col. 7, line 57, change "innocous" to --innocuous--.

In col. 7, line 65, change "anologous" to --analogous--.

In col. 8, line 32, change "forming" to --form--.

In col. 8, line 48, change "diagnosic" to --diagnosis--.

In col. 9, line 3, after "anhydride" insert a comma.

In col. 9, line 20, after "rabbits" insert --are--.

In col. 10, line 36, change "procaryotic" to --prokaryotic--.

In col. 12, line 14, after "plasmid" insert a comma.

In col. 12, line 31, after "yeast" insert a comma.

In col. 12, line 55, after "conditions" insert a comma.

UNITED STATES PATENT AND TRADEMARK OFFICE
CERTIFICATE OF CORRECTION

PATENT NO. : 4,742,003

DATED : 03 May 1988

INVENTOR(S) : R.M.A. DERYNCK and D.V. GOEDDEL

Page 3 of 5

It is certified that error appears in the above-identified patent and that said Letters Patent is hereby corrected as shown below:

In col. 14, line 18, change "binging" to --binding--.

In col. 14, line 36, change "anti-body" to --antibody--.

In col. 15, lines 27-28, change "on the" to --an--.

In col. 15, line 46, change "occuring" to --occurring--.

In col. 15, line 61, change "employ" to --employs--.

In col. 15, line 67, change "are" to --is--.

In col. 16, line 46, change "hydridization" to --hybridization--.

In col. 16, line 56, delete the comma (first occurrence).

In col. 17, line 1, after "D" insert a comma.

In col. 17, line 4, after "D" insert a comma.

In col. 17, line 14, change ",," to --,--.

In col. 17, line 23, after "to" insert --10--.

In col. 17, line 30, change "prodes" to --probes--.

In col. 17, line 31, after "Superfine" inset --column--.

In col. 17, lines 61-62, change "polyvinylpyrollidone" to --polyvinylpyrrolidone--.

In col. 17, line 62, after "albumin" insert --)--.

In col. 18, line 18, after "D" insert a comma.

UNITED STATES PATENT AND TRADEMARK OFFICE
CERTIFICATE OF CORRECTION

PATENT NO. : 4,742,003

DATED : 03 May 1988

INVENTOR(S) : R.M.A. DERYNCK and D.V. GOEDDEL

It is certified that error appears in the above-identified patent and that said Letters Patent is hereby corrected as shown below:

In col. 18, line 23, change "This" to --These--.

In col. 18, line 48, after "TGF-α" insert a comma.

In col. 20, line 16, change "oglionucleotide" to --oligonucleotide--.

In col. 20, line 64, change "of" to a comma and "rate" to --rat--.

In col. 22, line 33, after the parenthetical expression insert a comma.

In col. 23, line 10, change "was" to --were--.

In col. 23, line 11, change "site" to --sites--.

In col. 23, line 20, change the comma to a period.

In col. 23, line 47, delete the comma.

In col. 24, line 10, change "Hcl" to --HCl--.

In col. 24, line 15, change "fives" to --gives--.

In col. 24, line 32, after "plasmids" insert a comma.

In col. 24, line 42, change "toethnol" to --toethanol--.

In col. 24, line 46, change "μ" to --β--.

In col. 24, line 55, change "was" to --were--.

In col. 25, line 55, change "(o)" (first occurrence) to --(open circle)-- and "(o)" (second occurrence) to --(closed circle)--.

In col. 26, line 47, after "4049" insert --)--.

UNITED STATES PATENT AND TRADEMARK OFFICE
CERTIFICATE OF CORRECTION

PATENT NO. : 4,742,003

DATED : 03 May 1988

INVENTOR(S) R.M.A. DERYNCK and D.V. GOEDDEL

It is certified that error appears in the above-identified patent and that said Letters Patent is hereby corrected as shown below:

In col. 26, line 48, change "plasid" to --plasmid--.

In col. 26, line 58, change "10)," to --10)--.

In col. 27, lines 35-36, after "mixture" insert --was--.

In col. 27, line 36, after "bacteria" insert --were--.

In col. 27, at reference 1, line 45, after "75" insert --,4001--.
In col. 27, at reference 7, line 56, change "Mozes" to --Moses--.
In col. 28, at reference 26, line 17, change "327" to --372--.

In col. 30, line 16, in claim 4, after "at" insert --the--.

Signed and Sealed this

Twenty-first Day of February, 1989

Attest:

DONALD J. QUIGG

Attesting Officer

Commissioner of Patents and Trademarks